(12) United States Patent
Ost et al.

(10) Patent No.: US 9,822,394 B2
(45) Date of Patent: Nov. 21, 2017

(54) NUCLEIC ACID SAMPLE PREPARATION

(71) Applicant: Cambridge Epigenetix Limited, Cambridge (GB)

(72) Inventors: Tobias William Barr Ost, Cambridge (GB); Neil Matthew Bell, Cambridge (GB)

(73) Assignee: CAMBRIDGE EPIGENETIX LIMITED (GB)

( * ) Notice: Subject to any disclaimer, the term of this patent is extended or adjusted under 35 U.S.C. 154(b) by 0 days.

(21) Appl. No.: 15/054,227

(22) Filed: Feb. 26, 2016

(65) Prior Publication Data

US 2016/0251700 A1  Sep. 1, 2016

Related U.S. Application Data

(63) Continuation of application No. PCT/GB2015/050525, filed on Feb. 24, 2015.

(30) Foreign Application Priority Data

Feb. 24, 2014 (GB) .................................. 1403216.3

(51) Int. Cl.
 *C12Q 1/68* (2006.01)
(52) U.S. Cl.
 CPC .......... *C12Q 1/6806* (2013.01); *C12Q 1/6855* (2013.01); *C12Q 1/6869* (2013.01); *C12Q 1/6874* (2013.01)
(58) Field of Classification Search
 CPC combination set(s) only.
 See application file for complete search history.

(56) References Cited

U.S. PATENT DOCUMENTS

| | | | |
|---|---|---|---|
| 6,114,149 A | 9/2000 | Fry et al. | |
| 8,741,567 B2 | 6/2014 | He et al. | |
| 9,115,386 B2 | 8/2015 | Rao et al. | |
| 9,175,348 B2 | 11/2015 | Korlach et al. | |
| 9,290,807 B2 | 3/2016 | Booth et al. | |
| 9,297,806 B2 | 3/2016 | Yegnasubramanian et al. | |
| 9,447,452 B2 | 9/2016 | Rao et al. | |
| 9,611,510 B2 | 4/2017 | He et al. | |
| 2004/0038215 A1 | 2/2004 | Kumar et al. | |
| 2004/0132026 A1 | 7/2004 | Olek | |
| 2005/0037393 A1* | 2/2005 | Gunderson | C12Q 1/6827 435/6.11 |
| 2005/0287592 A1 | 12/2005 | Kless | |
| 2009/0068659 A1* | 3/2009 | Taylor | C12Q 1/6874 435/6.12 |
| 2009/0088327 A1* | 4/2009 | Rigatti | C12Q 1/6874 506/4 |
| 2009/0325169 A1* | 12/2009 | Walder | C12Q 1/6844 435/6.18 |
| 2014/0030727 A1 | 1/2014 | Pfeifer et al. | |
| 2014/0228231 A1 | 8/2014 | Vilain et al. | |
| 2014/0274729 A1* | 9/2014 | Kurn | B01J 19/0046 506/2 |
| 2014/0363815 A1 | 12/2014 | Dahl et al. | |
| 2015/0056616 A1 | 2/2015 | He et al. | |
| 2015/0299781 A1 | 10/2015 | Ost | |
| 2016/0186207 A1 | 6/2016 | Reik et al. | |
| 2016/0222448 A1 | 8/2016 | Horvath | |
| 2016/0258014 A1 | 9/2016 | Booth et al. | |
| 2017/0145484 A1 | 5/2017 | Rao et al. | |

FOREIGN PATENT DOCUMENTS

| | | |
|---|---|---|
| CN | 105648537 A | 6/2016 |
| EP | 1320632 B1 | 6/2006 |
| EP | 2694686 A2 | 2/2014 |
| EP | 2791361 A1 | 10/2014 |
| EP | 3061764 A1 | 8/2016 |
| WO | 03050242 | 6/2003 |
| WO | 2005010159 | 2/2005 |
| WO | WO-2010037001 A2 | 4/2010 |
| WO | 2010094040 | 8/2010 |
| WO | WO-2013017853 A2 | 2/2013 |
| WO | WO-2014083118 A1 | 6/2014 |
| WO | WO-2015043493 A1 | 4/2015 |
| WO | WO-2015048665 A2 | 4/2015 |
| WO | WO-2015124955 A1 | 8/2015 |
| WO | WO-2015145133 A1 | 10/2015 |
| WO | WO-2016016639 A1 | 2/2016 |
| WO | WO-2016034908 A1 | 3/2016 |
| WO | WO-2016063034 A1 | 4/2016 |
| WO | WO-2016063059 A1 | 4/2016 |
| WO | WO-2016079509 A1 | 5/2016 |

(Continued)

OTHER PUBLICATIONS

Horspool et al., "Efficient assembly of very short oligonucleotides using T4 DNA Ligase", BMC Research Notes, 2010, 3:291, 1-9.
Li et al., "Structure-independent and quantitative ligation of single-stranded DNA", Anal Biochem, 2006, 349:242-246.
Schmidt et al., "5'-triphosphate RNA requires base-paired structures to activate antiviral signaling via RIG-I", Proc Natl Acad Sci, 2009, 106:12067-72.
Liu et al., "Development and validation of a T7 based linear amplification for genomic DNA", BMC Genomics, 2003, 4:19.
Motea et al., "Terminal deoxynucleotidyl transferase: the story of a misguided DNA polymerase", Biochim Biophys Acta, 2010, 1804:1151-66.

(Continued)

*Primary Examiner* — Jennifer Dunston

(74) *Attorney, Agent, or Firm* — Wilson Sonsini Goodrich & Rosati

(57) ABSTRACT

This invention relates to the preparation of nucleic acid samples for analysis. The invention may be particularly useful for single stranded samples. Embodiments of the invention involve the attachment of double stranded or hairpin oligonucleotides using template independent polymerase enzymes in the preparation of nucleic acid sequencing libraries.

14 Claims, 13 Drawing Sheets

(56) References Cited

FOREIGN PATENT DOCUMENTS

| WO | WO-2016170319 A1 | 10/2016 |
| WO | WO-2016189288 A1 | 12/2016 |

OTHER PUBLICATIONS

Monroy et al., "Characteristics of reactions catalyzed by purified guanylyltransferase from vaccinia virus", Journal of Biological Chemistry, 1978, 253:4490-4498.
Sorensen et al., "Enzymatic ligation of large biomolecules to DNA", ACS Nano, 2013, 7:8098-8104.
Kuhn et al., "Template-independent ligation of single-stranded DNA by T4 DNA ligase", FEBS Journal, 2005, 272:5991-6000.
Booth, et al. Quantitative sequencing of 5-methylcytosine and 5-hydroxymethylcytosine at single-base resolution. Science. May 18, 2012;336(6083):934-7. doi: 10.1126/science.1220671. Epub Apr. 26, 2012. Abstract only.
Booth, M.J., et al. (2013). Oxidative Bisulfite Sequencing of 5-Methylcytosine and 5-Hydroxymethylcytosine. Nat. Protoc. 8, 1841-1851.
Clark, et al. Enhanced 5-methylcytosine detection in single-molecule, real-time sequencing via Tet1 oxidation. BMC Biol. Jan. 22, 2013;11:4. doi: 10.1186/1741-7007-11-4.
Co-pending U.S. Appl. No. 15/128,472, filed Sep. 23, 2016.
Co-pending U.S. Appl. No. 15/328,212, filed Jan. 23, 2017.
Co-pending U.S. Appl. No. 15/508,520, filed Mar. 3, 2017.
Ficz, et al. Reprogramming by cell fusion: boosted by Tets. Mol Cell. Mar. 28, 2013;49(6):1017-8. doi: 10.1016/j.molcel.2013.03.014.
Final Office Action dated Jan. 5, 2014 for U.S. Appl. No. 13/120,861.
Final Office Action dated Aug. 25, 2014 for U.S. Appl. No. 13/795,739.
Flusberg, et al. Direct detection of DNA methylation during single-molecule, real-time sequencing. Nat Methods. Jun. 2010;7(6):461-5. doi: 10.1038/nmeth.1459. Epub May 9, 2010.
Fu, Y. et al. (2012). Nucleic Acid Modifications With Epigenetic Significance. Curr. Opin. Chem. Biol. 16, 516-524.
He, et al. Tet-mediated formation of 5-carboxylcytosine and its excision by TDG in mammalian DNA. Science. Sep. 2, 2011;333(6047):1303-7. doi: 10.1126/science.1210944. Epub Aug. 4, 2011.
International search report with written opinion dated Jul. 16, 2015 for PCT/GB2015/050525.
Ito, et al. Tet proteins can convert 5-methylcytosine to 5-formylcytosine and 5-carboxylcytosine. Science. Sep. 2, 2011;333(6047):1300-3. doi: 10.1126/science.1210597. Epub Jul. 21, 2011.
Johnson, et al. 5-Hydroxymethylcytosine localizes to enhancer elements and is associated with survival in glioblastoma patients. Nat Commun. Nov. 25, 2016;7:13177. doi: 10.1038/ncomms13177.
Kawasaki, et al. A Novel method for the simultaneous identification of methylcytosine and hydroxymethylcytosine at a single base resolution. Nucleic Acids Res. Oct. 24, 2016. pii: gkw994. [Epub ahead of print].
Mellen, M., et al. (2012). MeCP2 binds to 5hmC enriched within active genes and accessible chromatin in the nervous system. Cell 151, 1417-1430.
Non-Final Office Action dated Apr. 8, 2015 for U.S. Appl. No. 14/235,707.
Non-Final Office Action dated Aug. 9, 2014 for U.S. Appl. No. 13/120,861.
Non-Final Office Action dated Mar. 13, 2013 for U.S. Appl. No. 13/120,861.
Non-Final Office Action dated Sep. 16, 2013 for U.S. Appl. No. 13/120,861.
Non-Final Office Action dated Sep. 17, 2015 for U.S. Appl. No. 13/795,739.
Non-Final Office Action dated Mar. 24, 2014 for U.S. Appl. No. 13/795,739.
Pacific Biosciences. Detecting DNA Base Modification Using Single Molecule, Real-Time Sequencing. Copyright 2012. printed as pp. 1/5-5/5.
Rodic, et al. Diagnostic utility of 5-hydroxymethylcytosine immunohistochemistry in melanocytic proliferations. J Cutan Pathol. Nov. 2015;42(11):807-14. doi: 10.1111/cup.12564. Epub Sep. 2, 2015.
Seisenberger, S., et al. (2012). The dynamics of genome-wide DNA methylation reprogramming in mouse primordial germ cells. Mol. Cell 48, 849-862.
Song, et al. Simultaneous single-molecule epigenetic imaging of DNA methylation and hydroxymethylation. Proc Natl Acad Sci U S A. Apr. 19, 2016;113(16):4338-43. doi: 10.1073/pnas.1600223113. Epub Mar. 28, 2016.
Xia, et al. Bisulfite-free, base-resolution analysis of 5-formylcytosine at the genome scale. Nat Methods. Nov. 2015;12(11):1047-50. doi: 10.1038/nmeth.3569. Epub Sep. 7, 2015.
Yu, et al. Base-resolution analysis of 5-hydroxymethylcytosine in the mammalian genome. Cell. Jun. 8, 2012;149(6):1368-80. doi: 10.1016/j.cell.2012.04.027. Epub May 17, 2012.
Yu, et al. Tet-assisted bisulfite sequencing of 5-hydroxymethylcytosine. Nat Protoc. Dec. 2012;7(12):2159-70. doi: 10.1038/nprot.2012.137. Epub Nov. 29, 2012.
Tomaschewski, et al. T4-induced alpha-and beta-glucosyltransferase: cloning of the genes and a comparison of their products based on sequencing data. Nucleic Acids Res. Nov. 11, 1985; 13(21): 7551-7568.

\* cited by examiner

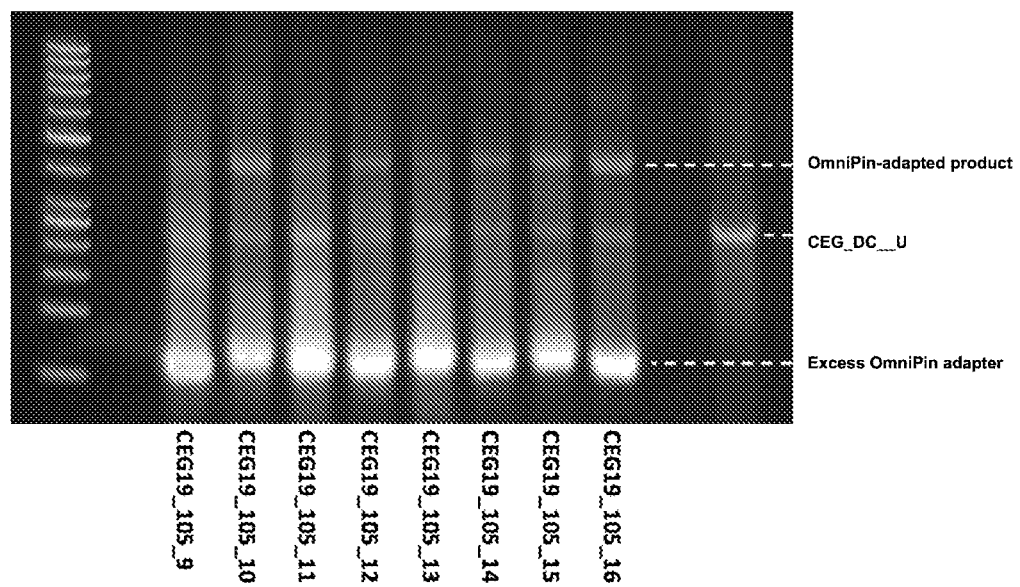
Figure 12: 4-20% PAGE TBE gel of OmniPin (hairpin)-adapted templates

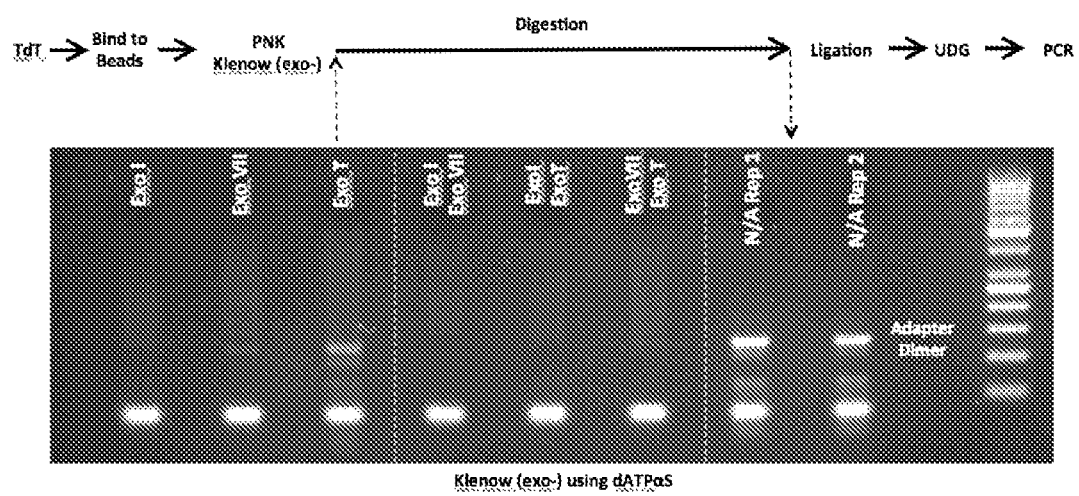
Figure 13. 2% agarose gel showing the PCR-amplified OmniPrep libraries

SEQUENCE LISTING

```
<160> NUMBER OF SEQ ID NOS: 20

<210> SEQ ID NO 1
<211> LENGTH: 100
<212> TYPE: DNA
<213> ORGANISM: Artificial Sequence
<220> FEATURE:
<221> NAME/KEY: misc_feature
<222> LOCATION: 1..100
<223> OTHER INFORMATION: synthetic oligonucleotide
<220> FEATURE:
<221> NAME/KEY: misc_feature
<222> LOCATION: 1
<223> OTHER INFORMATION: /note="Fluorescein (FAM) label"

<400> SEQUENCE: 1
ctcacccaca accacaaaca tacgatcacg gcgaatccga tcgaatcagt tccgcgcttt    60
```
atgaagtgcg acagccttag tgatgtgatg ggtggtatgg                          100

<210> SEQ ID NO 2
<211> LENGTH: 100
<212> TYPE: DNA
<213> ORGANISM: Artificial Sequence
<220> FEATURE:
<221> NAME/KEY: misc_feature
<222> LOCATION: 1..100
<223> OTHER INFORMATION: synthetic oligonucleotide
<220> FEATURE:
<221> NAME/KEY: misc_feature
<222> LOCATION: 99,100
<223> OTHER INFORMATION: /note="n is a or g or c or t/u, unknown, or other"
<220> FEATURE:
<221> NAME/KEY: misc_feature
<222> LOCATION: 1
<223> OTHER INFORMATION: /note="c is c-phosphate"

<400> SEQUENCE: 2
ctcacccaca accacaaaca taugatauaug gugaatuuga tugaatuagt tuuguguttt    60
augaagtgug auaguuttag tgatgtgatg ggtggtatnn                          100

<210> SEQ ID NO 3
<211> LENGTH: 83
<212> TYPE: DNA
<213> ORGANISM: Artificial Sequence
<220> FEATURE:
<221> NAME/KEY: misc_feature
<222> LOCATION: 1..83
<223> OTHER INFORMATION: synthetic oligonucleotide
<220> FEATURE:
<221> NAME/KEY: misc_feature
<222> LOCATION: 78..83
<223> OTHER INFORMATION: /note="h is a or c or t/u"
<220> FEATURE:
<221> NAME/KEY: misc_feature
<222> LOCATION: 1
<223> OTHER INFORMATION: /note="DiBenzoCycloOctyne-Adapter"
<220> FEATURE:
<221> NAME/KEY: misc_feature
<222> LOCATION: 83
<223> OTHER INFORMATION: /note="h is h-phosphate"

<400> SEQUENCE: 3
gatcggaaga gcucaagcag aagacggcat acgagatcgt gatgtgactg gagttcagac    60
gtgtgctctt ccgatcthhh hhh                                            83

<210> SEQ ID NO 4
<211> LENGTH: 83
<212> TYPE: DNA
<213> ORGANISM: Artificial Sequence
<220> FEATURE:
<221> NAME/KEY: misc_feature
<222> LOCATION: 1..83
<223> OTHER INFORMATION: synthetic oligonucleotide
<220> FEATURE:
<221> NAME/KEY: misc_feature
<222> LOCATION: 78..83
<223> OTHER INFORMATION: /note="h is a or c or t/u"
<220> FEATURE:
<221> NAME/KEY: misc_feature
<222> LOCATION: 1
<223> OTHER INFORMATION: /note="DiBenzoCycloOctyne-Adapter"
<220> FEATURE:
<221> NAME/KEY: misc_feature
<222> LOCATION: 83
<223> OTHER INFORMATION: /note="h is h-phosphate"

<400> SEQUENCE: 4

```
gatcggaaga gcucaagcag aagacggcat acgagattgg tcagtgactg gagttcagac    60
gtgtgctctt ccgatcthhh hhh                                            83
```

<210> SEQ ID NO 5
<211> LENGTH: 83
<212> TYPE: DNA
<213> ORGANISM: Artificial Sequence
<220> FEATURE:
<221> NAME/KEY: misc_feature
<222> LOCATION: 1..83
<223> OTHER INFORMATION: synthetic oligonucleotide
<220> FEATURE:
<221> NAME/KEY: misc_feature
<222> LOCATION: 78..83
<223> OTHER INFORMATION: /note="h is a or c or t/u"
<220> FEATURE:
<221> NAME/KEY: misc_feature
<222> LOCATION: 1
<223> OTHER INFORMATION: /note="DiBenzoCycloOctyne-Adapter"
<220> FEATURE:
<221> NAME/KEY: misc_feature
<222> LOCATION: 83
<223> OTHER INFORMATION: /note="h is h-phosphate"

<400> SEQUENCE: 5

```
gatcggaaga gcucaagcag aagacggcat acgagatcac tgtgtgactg gagttcagac    60
gtgtgctctt ccgatcthhh hhh                                            83
```

<210> SEQ ID NO 6
<211> LENGTH: 83
<212> TYPE: DNA
<213> ORGANISM: Artificial Sequence
<220> FEATURE:
<221> NAME/KEY: misc_feature
<222> LOCATION: 1..83
<223> OTHER INFORMATION: synthetic oligonucleotide
<220> FEATURE:
<221> NAME/KEY: misc_feature
<222> LOCATION: 78..83
<223> OTHER INFORMATION: /note="h is a or c or t/u"
<220> FEATURE:
<221> NAME/KEY: misc_feature
<222> LOCATION: 1
<223> OTHER INFORMATION: /note="DiBenzoCycloOctyne-Adapter"
<220> FEATURE:
<221> NAME/KEY: misc_feature
<222> LOCATION: 83
<223> OTHER INFORMATION: /note="h is h-phosphate"

<400> SEQUENCE: 6

```
gatcggaaga gcucaagcag aagacggcat acgagatatt ggcgtgactg gagttcagac    60
gtgtgctctt ccgatcthhh hhh                                            83
```

<210> SEQ ID NO 7
<211> LENGTH: 83
<212> TYPE: DNA
<213> ORGANISM: Artificial Sequence
<220> FEATURE:
<221> NAME/KEY: misc_feature
<222> LOCATION: 1..83
<223> OTHER INFORMATION: synthetic oligonucleotide
<220> FEATURE:
<221> NAME/KEY: misc_feature
<222> LOCATION: 78..83
<223> OTHER INFORMATION: /note="h is a or c or t/u"
<220> FEATURE:
<221> NAME/KEY: misc_feature
<222> LOCATION: 1
<223> OTHER INFORMATION: /note="DiBenzoCycloOctyne-Adapter"
<220> FEATURE:

<221> NAME/KEY: misc_feature
<222> LOCATION: 83
<223> OTHER INFORMATION: /note="h is h-phosphate"

<400> SEQUENCE: 7
gatcggaaga gcucaagcag aagacggcat acgagataca tcggtgactg gagttcagac    60
gtgtgctctt ccgatcthhh hhh                                            83

<210> SEQ ID NO 8
<211> LENGTH: 83
<212> TYPE: DNA
<213> ORGANISM: Artificial Sequence
<220> FEATURE:
<221> NAME/KEY: misc_feature
<222> LOCATION: 1..83
<223> OTHER INFORMATION: synthetic oligonucleotide
<220> FEATURE:
<221> NAME/KEY: misc_feature
<222> LOCATION: 78..83
<223> OTHER INFORMATION: /note="h is a or c or t/u"
<220> FEATURE:
<221> NAME/KEY: misc_feature
<222> LOCATION: 1
<223> OTHER INFORMATION: /note="DiBenzoCycloOctyne-Adapter"
<220> FEATURE:
<221> NAME/KEY: misc_feature
<222> LOCATION: 83
<223> OTHER INFORMATION: /note="h is h-phosphate"

<400> SEQUENCE: 8
gatcggaaga gcucaagcag aagacggcat acgagatgcc taagtgactg gagttcagac    60
gtgtgctctt ccgatcthhh hhh                                            83

<210> SEQ ID NO 9
<211> LENGTH: 83
<212> TYPE: DNA
<213> ORGANISM: Artificial Sequence
<220> FEATURE:
<221> NAME/KEY: misc_feature
<222> LOCATION: 1..83
<223> OTHER INFORMATION: synthetic oligonucleotide
<220> FEATURE:
<221> NAME/KEY: misc_feature
<222> LOCATION: 78..83
<223> OTHER INFORMATION: /note="h is a or c or t/u"
<220> FEATURE:
<221> NAME/KEY: misc_feature
<222> LOCATION: 1
<223> OTHER INFORMATION: /note="DiBenzoCycloOctyne-Adapter"
<220> FEATURE:
<221> NAME/KEY: misc_feature
<222> LOCATION: 83
<223> OTHER INFORMATION: /note="h is h-phosphate"

<400> SEQUENCE: 9
gatcggaaga gcucaagcag aagacggcat acgagattac aaggtgactg gagttcagac    60
gtgtgctctt ccgatcthhh hhh                                            83

<210> SEQ ID NO 10
<211> LENGTH: 83
<212> TYPE: DNA
<213> ORGANISM: Artificial Sequence
<220> FEATURE:
<221> NAME/KEY: misc_feature
<222> LOCATION: 1..83
<223> OTHER INFORMATION: synthetic oligonucleotide
<220> FEATURE:
<221> NAME/KEY: misc_feature
<222> LOCATION: 78..83
<223> OTHER INFORMATION: /note="h is a or c or t/u"

```
<220> FEATURE:
<221> NAME/KEY: misc_feature
<222> LOCATION: 1
<223> OTHER INFORMATION: /note="DiBenzoCycloOctyne-Adapter"
<220> FEATURE:
<221> NAME/KEY: misc_feature
<222> LOCATION: 83
<223> OTHER INFORMATION: /note="h is h-phosphate"

<400> SEQUENCE: 10
gatcggaaga gcucaagcag aagacggcat acgagatttt cacgtgactg gagttcagac      60
gtgtgctctt ccgatcthhh hhh                                              83

<210> SEQ ID NO 11
<211> LENGTH: 58
<212> TYPE: DNA
<213> ORGANISM: Artificial Sequence
<220> FEATURE:
<221> NAME/KEY: misc_feature
<222> LOCATION: 1..58
<223> OTHER INFORMATION: synthetic oligonucleotide

<400> SEQUENCE: 11
aatgatacgg cgaccaccga gatctacact ctutccctac acgacgctct uccgatct        58

<210> SEQ ID NO 12
<211> LENGTH: 57
<212> TYPE: DNA
<213> ORGANISM: Artificial Sequence
<220> FEATURE:
<221> NAME/KEY: misc_feature
<222> LOCATION: 1..57
<223> OTHER INFORMATION: synthetic oligonucleotide
<220> FEATURE:
<221> NAME/KEY: misc_feature
<222> LOCATION: 1
<223> OTHER INFORMATION: /note="g is g-phosphate"
<220> FEATURE:
<221> NAME/KEY: misc_feature
<222> LOCATION: 57
<223> OTHER INFORMATION: /note="t is t-phosphate"

<400> SEQUENCE: 12
gatcggaaga gcgtcgtgta gggaaagagt gtagatctcg gtggtcgccg tatcatt         57

<210> SEQ ID NO 13
<211> LENGTH: 21
<212> TYPE: DNA
<213> ORGANISM: Artificial Sequence
<220> FEATURE:
<221> NAME/KEY: misc_feature
<222> LOCATION: 1..21
<223> OTHER INFORMATION: synthetic oligonucleotide

<400> SEQUENCE: 13
aatgatacgg cgaccaccga g                                                21

<210> SEQ ID NO 14
<211> LENGTH: 21
<212> TYPE: DNA
<213> ORGANISM: Artificial Sequence
<220> FEATURE:
<221> NAME/KEY: misc_feature
<222> LOCATION: 1..21
<223> OTHER INFORMATION: synthetic oligonucleotide

<400> SEQUENCE: 14
caagcagaag acggcatacg a                                                21
```

```
<210> SEQ ID NO 15
<211> LENGTH: 53
<212> TYPE: DNA
<213> ORGANISM: Artificial Sequence
<220> FEATURE:
<221> NAME/KEY: misc_feature
<222> LOCATION: 1..53
<223> OTHER INFORMATION: synthetic oligonucleotide
<220> FEATURE:
<221> NAME/KEY: misc_feature
<222> LOCATION: 1
<223> OTHER INFORMATION: /note="DiBenzoCycloOctyne-Adapter"
<220> FEATURE:
<221> NAME/KEY: misc_feature
<222> LOCATION: 3
<223> OTHER INFORMATION: /note="biotin label"
<220> FEATURE:
<221> NAME/KEY: misc_feature
<222> LOCATION: 48..53
<223> OTHER INFORMATION: /note="h is a or c or t/u"
<220> FEATURE:
<221> NAME/KEY: misc_feature
<222> LOCATION: 53
<223> OTHER INFORMATION: /note="h is h-phosphate"

<400> SEQUENCE: 15
gatcggaaga gcutacactc tttccctaca cgacgctctt ccgatcthhh hhh          53

<210> SEQ ID NO 16
<211> LENGTH: 34
<212> TYPE: DNA
<213> ORGANISM: Artificial Sequence
<220> FEATURE:
<221> NAME/KEY: misc_feature
<222> LOCATION: 1..34
<223> OTHER INFORMATION: synthetic oligonucleotide
<220> FEATURE:
<221> NAME/KEY: misc_feature
<222> LOCATION: 34
<223> OTHER INFORMATION: /note="t is t-phosphate"

<400> SEQUENCE: 16
gtgactggag tucagacgtg tgctctuccg atct                               34

<210> SEQ ID NO 17
<211> LENGTH: 33
<212> TYPE: DNA
<213> ORGANISM: Artificial Sequence
<220> FEATURE:
<221> NAME/KEY: misc_feature
<222> LOCATION: 1..33
<223> OTHER INFORMATION: synthetic oligonucleotide
<220> FEATURE:
<221> NAME/KEY: misc_feature
<222> LOCATION: 1,33
<223> OTHER INFORMATION: /note="g is g-phosphate; c is c-phosphate"

<400> SEQUENCE: 17
gatcggaaga gcacacgtct gaactccagt cac                                33

<210> SEQ ID NO 18
<211> LENGTH: 58
<212> TYPE: DNA
<213> ORGANISM: Artificial Sequence
<220> FEATURE:
<221> NAME/KEY: misc_feature
<222> LOCATION: 1..58
<223> OTHER INFORMATION: synthetic oligonucleotide

<400> SEQUENCE: 18
aatgatacgg cgaccaccga gatctacact ctttccctac acgacgctct tccgatct     58
```

```
<210> SEQ ID NO 19
<211> LENGTH: 51
<212> TYPE: DNA
<213> ORGANISM: Artificial Sequence
<220> FEATURE:
<221> NAME/KEY: misc_feature
<222> LOCATION: 1..51
<223> OTHER INFORMATION: synthetic oligonucleotide

<400> SEQUENCE: 19
caagcagaag acggcatacg agatcactgt gtgactggag ttcagacgtg t          51

<210> SEQ ID NO 20
<211> LENGTH: 21
<212> TYPE: DNA
<213> ORGANISM: Artificial Sequence
<220> FEATURE:
<221> NAME/KEY: misc_feature
<222> LOCATION: 1..21
<223> OTHER INFORMATION: synthetic oligonucleotide

<400> SEQUENCE: 20
agatcggaag agcacacgtc t                                           21
```

NUCLEIC ACID SAMPLE PREPARATION

CROSS REFERENCE TO RELATED APPLICATIONS

The present application is a Continuation Application of co-pending International Application No. PCT/GB2015/050525, filed Feb. 24, 2015, which in turn claims priority from Great Britain Application No. 1403216.3, filed Feb. 24, 2014. Applicants claim the benefits of 35 U.S.C. §120 as to the PCT application and priority under 35 U.S.C. §119 as to the Great Britain application, and the entire disclosure of each application is incorporated herein by reference in its entirety.

This invention relates to the preparation of nucleic acid samples for analysis.

Many methods exist for the preparation of samples of double-stranded DNA, for example for sequencing (e.g. Illumina TruSeq and NextEra, 454, NEBnext, Life Technologies etc).

However, the preparation of single-stranded DNA samples is more challenging because single stranded DNA molecules cannot be efficiently ligated together enzymatically. Reported workflows for the preparation of single-stranded DNA rely on the use of primers with degenerate sequences that "randomly prime" the single-stranded DNA and allow a truncated version of the parent DNA molecule to be adapted (for example, EPIGENOME™ Methyl-Seq kit, Epicentre Technologies Wis. USA). Methods using RNA ligase or CIRCLIGASE™ to join ends of single stranded DNA together have been reported but suffer from poor efficiency or are limited to the size of DNA fragments that can be ligated together.

Single stranded sample preparation is commonly used following bisulfite conversion of DNA molecules. The bisulfite conversion process necessarily results in the formation of single stranded DNA, and therefore involves either i) pre-bisulfite sample preparation or ii) post-bisulfite sample preparation employing random priming for downstream analysis. Drawbacks to these methods include the potential to generate nicked or fragmented libraries incapable of subsequent amplification, the loss of sequence information from the parent DNA molecules, generation of artefacts that contaminate the sample of interest or induce significant representation bias of reads in the final dataset. A direct method of ligating the termini of single stranded DNA post-bisulfite treatment in quantitative yield is of significant interest.

An aspect of the invention described herein provides a method of joining two oligonucleotides using a template independent nucleic acid polymerase enzyme such as terminal deoxynucleotidyl transferase (TdT). Terminal deoxynucleotidyl transferase (TdT), also known as DNA nucleotidylexotransferase (DNTT) or terminal transferase, is a specialized DNA polymerase which catalyses the addition of nucleotides to the 3' terminus of a DNA molecule. Unlike most DNA polymerases, it does not require a template. TdT typically adds nucleotide 5-triphosphates onto the 3'-hydroxyl of a single stranded first oligonucleotide sequence. The invention as described herein uses a second oligonucleotide carrying a 5'-triphosphosphate which can be attached to the first oligonucleotide sequence, thus enabling two single stranded oligonucleotides to be joined together, catalysed by TdT. Thus the enzyme can be used to link two oligonucleotide strands, rather than simply adding individual nucleotides.

An aspect of the invention described herein includes the attachment of adapters to single stranded nucleic acid samples. The adapters are oligonucleotides having a 5'-triphosphate and a 3' single stranded 'overhang' region which hybridises to the ends of the nucleic acid sample. The adapters may be in the form of single stranded 'hairpins' having portions of self-complementary sequences, such that the 5'-triphosphate and 3' single stranded 'overhang' region are within the same molecule, or may be two strands having at least partly complementary sequences, one strand having a 5'-triphosphate and the second strand having a 3' single stranded 'overhang' region. The adapters may be used to copy the single stranded samples by extension of the 3'-overhang, which is hybridised to the nucleic acid strands and acts as a primer. The attachment of the adapter may be carried out using a template independent polymerase or a template dependent polymerase.

Polyadenylate polymerase (PAP) is an enzyme involved in the formation of the polyadenylate tail of the 3' end of mRNA. PAP uses adenosine triphosphate (ATP) to add adenosine nucleotides to the 3' end of an RNA strand. The enzyme works in a template independent manner. A further aspect of the invention involves the use of PAP to join two oligonucleotides. In the use of PAP, one or more of the oligonucleotides may be RNA rather than DNA. Similarly poly(U) polymerase catalyzes the template independent addition of UMP from UTP or AMP from ATP to the 3' end of RNA.

The term template independent nucleic acid polymerase enzyme includes any polymerase which acts without requiring a nucleic acid template. The term template independent nucleic acid polymerase enzyme includes terminal deoxynucleotidyl transferase (TdT), Polyadenylate polymerase (PAP) and poly(U) polymerase (PUP). The template independent nucleic acid polymerase enzyme can be PAP. The template independent nucleic acid polymerase enzyme can be terminal transferase. The oligonucleotides joined can be RNA or DNA, or a combination of both RNA and DNA. The oligonucleotides can contain one or more modified backbone residues, modified sugar residues or modified nucleotide bases.

Template independent nucleic acid polymerase enzymes may be sensitive to the bulk of substituents attached to the ribose 3'-position. The standard substrates for these enzymes are nucleotide triphosphates in which the ribose 3'-position is a hydroxyl group. In order to increase the tolerance of the enzyme for sterically larger substituents at this position, the enzyme may be engineered using suitable amino acid substitutions to accommodate any increase in steric bulk. The term template independent nucleic acid polymerase enzyme therefore includes non-naturally occurring (engineered) enzymes. The term template independent nucleic acid polymerase enzyme includes modified versions of terminal transferase or PAP. Terminal transferase, PUP or PAP may be obtained from commercial sources (e.g. New England Biolabs).

The method described herein adds a single stranded oligonucleotide with a 3' hydroxyl to a single stranded oligonucleotide with a 5'-triphosphate moiety, as shown in FIG. 1. The triphosphate moiety can be attached directly to the 5'-hydroxyl of the second oligonucleotide. In such cases the 5'-oligonucleotide triphosphate can react directly with the 3'-hydroxyl group of the first oligonucleotide to form a single stranded oligonucleotide containing the first and second sequences linked together via a standard 'natural' phosphomonoester moiety. Such an oligonucleotide can be copied using a polymerase as there are no unnatural linking groups between the first and second oligonucleotides. The use of engineered template independent polymerase enzymes may increase the tolerance for steric bulk at the 3'-position of the triphosphate nucleotide, and hence allow the use of oligonucleotide strands attached directly to the 3'-hydroxl of a nucleotide triphosphate.

Alternatively the triphosphate can be attached through a linker moiety. Linker moieties can be any functionality attached to the terminal 5'hydroxyl of the oligonucleotide strand. The linker moiety can include one or more phosphate groups. The linker may contain a ribose or deoxyribose moiety. The linker may contain one or more further nucleotides. The nucleotides, or the ribose or deoxyribose moieties may be further substituted. The linker may contain a ribose or deoxyribose moiety in which the oligonucleotide is attached to the 2-position of the ribose. The linker may contain a nucleotide in which the remainder of the oligonucleotide is attached via the nucleotide base. Suitable linkers are shown in FIG. 2. Where the generic description 'linker' is used, the linker may employ one or more carbon, oxygen, nitrogen or phosphorus atoms. The linker acts merely to attach the functional triphosphate moiety to the remainder of the oligonucleotide.

The joined oligonucleotides may be copied using a nucleic acid polymerase. The linker should be able to permit a nucleotide polymerase to bridge though the linker in order to copy the strands after joining. The action of the polymerase may be enhanced by using a hybridised primer which can bridge across the linker region. The primer can be designed with a suitable length of sequence to space across the linker region. The sequence can be degenerate/random or simply be a suitable length of known sequence in order to bridge across any gap caused by the linker region.

The length of sequence used to bridge the gap can be designed depending on the choice of linker. The sequence can be used as a tag for individual fragments. The tag can be used to assess the level of bias introduced by any amplification reactions. If the tags are say 6 mers of random sequences, there at 4^6 (4096) different variants of different sequence. From a population of fragments from a biological sample, it is highly unlikely that two fragments of the same 'biological' sequence will be joined to a tag with the same 'tag' sequence. Therefore any examples where the fragments and tag are over-represented in the sequencing reaction occur because the particular individual fragment is over-amplified during the PCR reaction when compared to other fragments in the population. Thus the use of 'tags' of variable sequence can be used to help normalise the effects of amplification variability.

The tags can also be used to help identify sequences from different sources. If adapters are used with different sequences for different sources of biological materials, then the different sources can be pooled but still identified via the tag when the tags are sequenced. Thus the disclosure herein includes the use of two or more different populations of adapters for the multiplexing of the analysis of different samples. Disclosed herein therefore are kits containing two or more adapters of different sequence.

The oligonucleotide with the 5'-triphosphate may be blocked at the 3' end to prevent self joining. The blocking moiety may be a phosphate group or a similar moiety. Alternatively the 3' end may be a dideoxy nucleotide with no 3'-OH group.

The oligonucleotide with the 5'-triphosphate may be produced chemically or enzymatically. A suitable nucleotide 5'-triphosphate may be chemically coupled to a suitable oligonucleotide using suitable chemical couplings. For example, as shown in the examples, the nucleotide triphosphate may contain an azido ($N_3$) group and the oligonucleotide may contain an alkyne group. Alternatively a suitable oligonucleotide monophosphate may be turned into a triphosphate either chemically or enzymatically.

The sequence of the 5'-triphosphate adapter oligonucleotide depends on the specific application and suitable adapter oligonucleotides may be designed using known techniques. A suitable adapter oligonucleotide may, for example, consist of 20 to 100 nucleotides. The sequence of the adapter may be selected to be complementary to a suitable amplification/extension primer.

The second oligonucleotide, or oligonucleotide 5'-triphosphate adapter may be single stranded or double stranded. The double stranded adapter has at least one overhanging single stranded region, and may have two or three overhanging single stranded regions. The overhang serves to act to hybridise to the end of the single stranded nucleic acid to which the adapter is to be attached, and acts as a site which can undergo polymerase extension to make the attached single stranded sample molecules double stranded. The adapters can be 'forked' adapters having regions which are non-complementary as well as regions which are complementary.

Where the adapter is hybridised to the nucleic acid sample, the attachment of the adapter can be carried out using a template dependent polymerase. Any polymerase suitable for the incorporation of a nucleotide triphosphate can be used. The adapter can be thought of as a nucleotide triphosphate attached to an oligonucleotide duplex. Thus the adapter carries its own template.

The second oligonucleotide, or oligonucleotide 5'-triphosphate adapter may have a region of self-complementarity such that the second oligonucleotide may take the form of a hairpin. The hairpin may have 3'-overhang suitable for polymerase extension. The term single stranded therefore includes a single strand which is in part single stranded, and in part double stranded at certain temperatures, but which can be made single stranded by increasing the temperature.

The second oligonucleotide may have one or more regions for indexing such that different oligonucleotides can be attached to different samples, thereby allowing sample pooling.

The second oligonucleotide may have one or more modifications which allow site specific strand cleavage. The second oligonucleotide may have one or more uracil bases, thereby allowing site specific cleavage using enzyme treatment.

The second oligonucleotide may be attached to a solid surface, or may contain a modification allowing for subsequent immobilisation or capture. The joining reaction may be carried out on a solid support, or the joined products may be captured onto a surface after joining. The oligonucleotides may carry a moiety for surface capture, for example a biotin moiety. Alternatively the attachment may be covalent. The oligonucleotides may be immobilised on a solid support, and used to capture the single stranded oligonucleotide fragments.

The second oligonucleotide may be DNA, RNA or a mixture thereof. Where the adapter contains two strands, one strand may be DNA and one strand may be RNA.

Copies of the first single stranded oligonucleotides may be produced by extending the 3'-end of the attached adapter or hairpin. The extension of the adapter or hairpin produces an extended adapter or hairpin. Where the adapter is a hairpin, the extended hairpin can also be described as a double stranded nucleic acid having one end joined. Upon denaturation, the extended hairpin becomes a single stranded molecule, but the length of the double stranded portion (for example at least 100 base pairs) means that the sample rapidly hybridise to form the extended hairpin. The extension reaction may be carried out in solution, or on a solid support.

In the case where the second adapter is a hairpin, the adapter may be for example 5-20 bases of a first complementary sequence, a single stranded loop comprising a sequence that hybridises to the solid support and the sequencing primer (e.g. 50-70 nucleotides), optionally a unique index sequence (e.g. 6-10 nucleotides) and optionally one or more locations such as uracil for site specific cleavage, a second complementary sequence complementary to the first complementary sequence and optionally a 3' overhang (e.g. 1-10 bases). Thus the hairpin constructs may be 60 to 100 nucleotides or more in length.

The method may be used in order to prepare samples for nucleic acid sequencing. The method may be used to sequence a population of synthetic oligonucleotides, for example for the purposes of quality control. Alternatively, the first oligonucleotides may come from a population of nucleic acid molecules from a biological sample. The population may be fragments of between 100-10000 nucleotides in length. The fragments may be 200-1000 nucleotides in length. The fragments may be of random variable sequence. The order of bases in the sequence may be known, unknown, or partly known. The fragments may come from treating a biological sample to obtain fragments of shorter length than exist in the naturally occurring sample. The fragments may come from a random cleavage of longer strands. The fragments may be derived from treating a nucleic acid sample with a chemical reagent (for example sodium bisulfite, acid or alkali) or enzyme (for example with a restriction endonuclease or other nuclease). The fragments may come from a treatment step that causes double stranded molecules to become single stranded.

Methods of the invention may be useful in preparing a population of nucleic acid strands for sequencing, for example a population of bisulfite-treated single-stranded nucleic acid fragments. Bisulfite treatment produces single-stranded nucleic acid fragments, typically of about 250-1000 nucleotides in length. The population may be treated with bisulfite by incubation with bisulfite ions ($HSO_3^{2-}$). The use of bisulfite ions ($HSO_3^{2-}$) to convert unmethylated cytosines in nucleic acids into uracil is standard in the art and suitable reagents and conditions are well known. Numerous suitable protocols and reagents are also commercially available (for example, EpiTect™, Qiagen NL; EZ DNA Methylation™ Zymo Research Corp CA; CpGenome Turbo Bisulfite Modification Kit, Millipore; TrueMethyl™. Cambridge Epigenetix, UK. Bisulfite treatment converts cytosine and 5-formylcytosine residues in a nucleic acid strands into uracil. However, a small proportion of cytosine and 5-formylcytosine residues are eliminated by bisulfite treatment rather that converted to U, leading to the formation of abasic sites in the nucleic acid strands, which tends to cause strand cleavage.

The bisulfite solution may be provided in the form of sodium bisulfite, potassium bisulfite or ammonium bisulfite. Where the term bisulfite is used, the bisulfite may be obtained from any source, including metabisulfite. Thus the bisulfite may be provided by ammonium, sodium or potassium bisulfite or metabisulfite.

The sample may be compared with a sample which has not undergone bisulfite treatment. In such cases the sample may be prepared using alternative fragmentation methods, for example physical shearing followed by heat denaturation. Alternatively the sample may be compared with a sample which has undergone an alternative sample preparation method, for example double stranded ligation of adapters.

In other embodiments, a population of DNA strands having one or more abasic sites may be produced by subjecting a population of nucleic acid molecules to acid hydrolysis. The population may be subjected to acid hydrolysis by incubation at an acidic pH (for example, pH 5) and elevated temperature (for example, greater than 70° C.). A proportion of the purine bases in the nucleic acid strands will be lost, to generate abasic sites. The number of abasic sites formed depends on the pH, concentration of buffer, temperature and length of incubation.

In other embodiments, a population of DNA strands having one or more abasic sites may be produced by treating the population of nucleic acid strands with uracil-DNA glycosylase (UDG). The population may be treated with UDG by incubation with UDG at 37° C. UDG excises uracil residues in the nucleic acid strands leaving abasic sites. UDG may be obtained from commercial sources.

Disclosed herein is a method comprising;
a) providing a sample containing a population of nucleic acid molecules,
b) treating the population to produce a sample of DNA strands containing a mixture of first single stranded oligonucleotides of different sequence,
c) joining a second oligonucleotide sequence to the sample of DNA strands using template independent nucleic acid polymerase.

Disclosed herein is a method comprising;
a) providing a sample containing a population of nucleic acid molecules,
b) treating the population to produce a sample of DNA strands containing a mixture of first single stranded oligonucleotides of different sequence,
c) joining a second oligonucleotide sequence having a 5'-triphosphate to the sample of DNA strands.

A population of short duplex fragments can be made single stranded using suitable treatment steps, for example heat treatment.

The population of nucleic acid molecules may be a sample of DNA or RNA, for example a genomic DNA sample. Suitable DNA and RNA samples may be obtained or isolated from a sample of cells, for example, mammalian cells such as human cells or tissue samples, such as biopsies. In some embodiments, the sample may be obtained from a formalin fixed parafin embedded (FFPE) tissue sample. Suitable cells include somatic and germ-line cells.

The population may be a diverse population of nucleic acid molecules, for example a library, such as a whole genome library or a loci specific library.

Nucleic acid strands in the population may be amplified nucleic acid molecules, for example, amplified fragments of the same genetic locus or region from different samples.

Nucleic acid strands in the population may be enriched. For example, the population may be an enriched subset of a sample produced by pull-down onto a hybridisation array or digestion with a restriction enzyme.

Methods of the invention may be useful in producing populations of mono-adapted single stranded nucleic acid fragments i.e. nucleic acid strands having an adapter oligonucleotide attached to their 3' termini. In some embodiments, populations of 3' adapted single stranded nucleic acid fragments may be used directly for sequencing and/or amplification.

The sequence of the second oligonucleotide may be entirely known, or may include a variable region. The sequence may a universal sequence such that each joined sequence has a common 'adapter' sequence attached to one end. The attachment of an adapter to one end of a pool of fragments of variable sequence means that copies of the variable sequences can be produced using a single 'extension' primer.

If a single molecule sequencing technique is employed, the first oligonucleotide sequences may be determined by hybridising the joined fragments onto a solid support carrying an array of primers complementary to the second oligonucleotide sequence. Alternatively the joined fragments may have a modification at the 3'-end which allows attachment to a solid support.

The methods disclosed may further include the step of producing one or more copies of the first single stranded oligonucleotides. The methods may include producing multiple copies of each of the different sequences. The copies may be made by hybridising a primer sequence opposite a universal sequence on the second oligonucleotide sequence, and using a nucleic acid polymerase to synthesise a complementary copy of the first single stranded sequences. The production of the complementary copy provides a double stranded polynucleotide.

The double stranded polynucleotides can be amplified using primers complementary to both strands. The amplification can be locus-specific, as shown in FIG. 3. Locus specific amplification only amplifies a selection of the fragments in the pool and is therefore a selective amplification for certain sequences. Alternatively a third oligonucleotide sequence can be attached to the joined sequences. The attachment of the third sequence, which may be a second universal sequence, can allow amplification of all the fragments in the pool as each fragment possesses two universal ends.

Alternatively the double stranded polynucleotides may be made circular by attaching the ends together. In some embodiments, double stranded molecules produced by extension of a primer annealed to the adapter sequence may be circularised by ligation. This may be useful in the generation of circular nucleic acid constructs and plasmids or in the preparation of samples for sequencing using platforms that employ circular templates (e.g. PacBio SMRT sequencing). In some embodiments, populations of circularised 3' adapted nucleic acid fragments produced as described herein may be denatured and subjected to rolling circle or whole genome amplification using an amplification primer that hybridises to the 3'-adapter oligonucleotide to produce a population of concatomeric products. Amplification of circular fragments can be carried out using primers complementary to two regions of the single adapter sequence.

The third oligonucleotide may comprise a self-complementary double stranded region. The third oligonucleotide may be attached via ligation using a ligase. Alternatively the third oligonucleotide may be attached using a template independent polymerase as described herein. The attachment can be via blunt end ligation onto both strands of the extended duplex. Alternatively the ligation may be cohesive ligation using one or more overhanging complementary bases. Cohesive ligation may be used to help prevent adapter to adapter ligation. Cohesive ligation includes having a single base extension (a one base overhang).

The one base overhang on the adapters means the ends of the adapters can not ligate to each other.

An alternative to locus specific amplification is the use of random priming. Random priming is used in techniques such as whole genome amplification (WGA). Having a universal primer on one end of a population of single stranded fragments and a random primer on the opposite end means that amplification is more efficient than having random primers on both ends, as is the case with WGA.

Described herein are kits and components for carrying out the invention. Disclosed is a kit for use in preparing a nucleic acid sample, the kit comprising a single stranded polynucleotide having a triphosphate moiety at the 5'-end and a terminal transferase. The kit may contain a nucleotide 5-triphosphate adapter having any of the features described herein. The adapter may be in the form of a hairpin. Disclosed herein are kits containing two or more oligonucleotide adapters of different sequence, each having a nucleotide 5-triphosphate. The two or more different sequences may include a fixed sequence capable of hybridising to an extension primer, and a variable sequence which acts as a tag to identify the adapter (and hence the identify of the sample to which the adapters are attached).

The invention includes a single stranded oligonucleotide comprising a triphosphate moiety attached to the 5'-end via a linker. The oligonucleotide may have any of the features described herein. The oligonucleotide may be in the form of a hairpin. The linker may contain a nucleotide in which the remainder of the oligonucleotide is attached via the nucleotide base.

Certain aspects and embodiments of the invention will now be illustrated by way of example and with reference to the figures described below.

Figure 1:
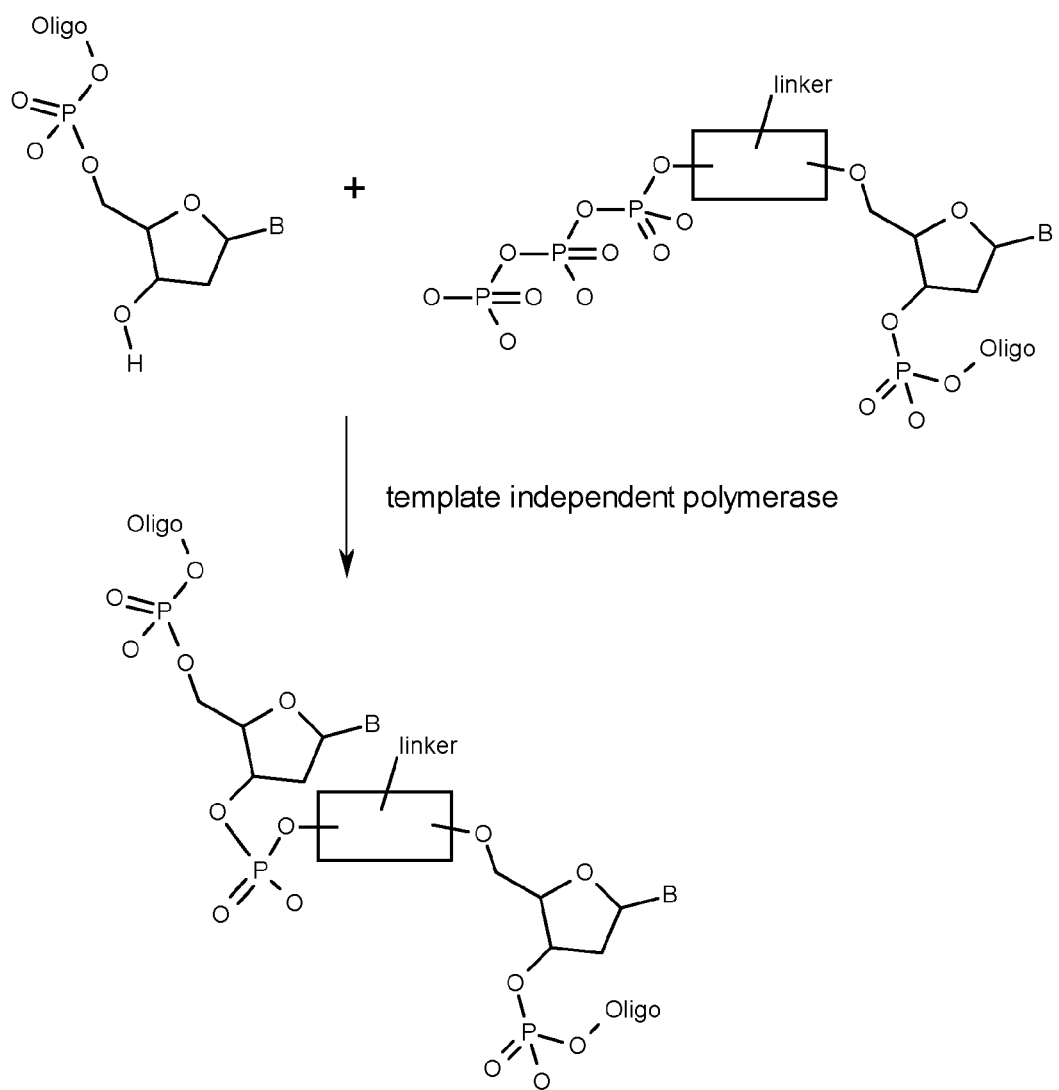
FIG. 1 shows the joining of two oligonucleotide strands using a template independent polymerase. The use of DNA is shown, but the oligonucleotide could be RNA, DNA or a hybrid thereof.
Figure 2:
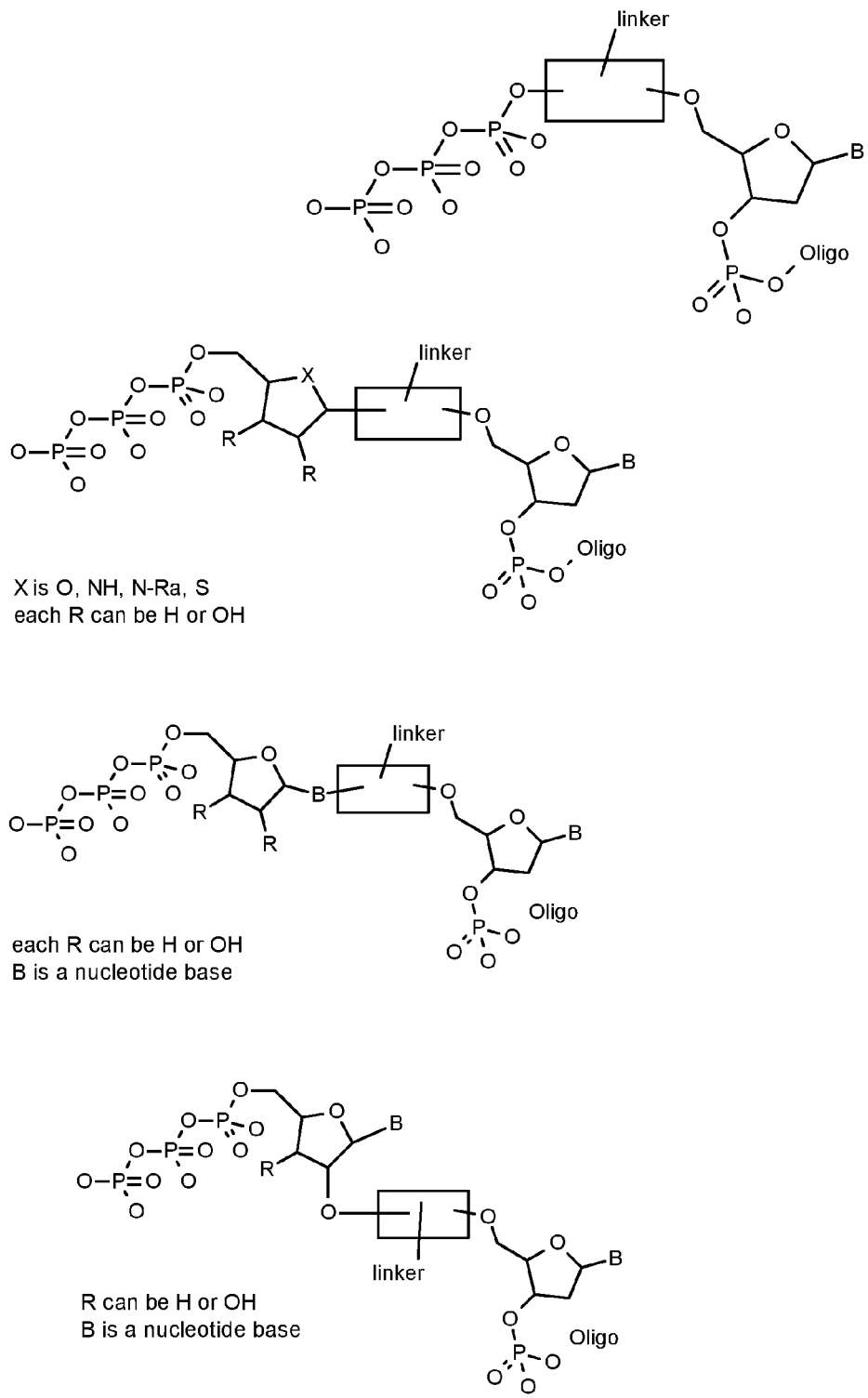
FIG. 2 shows a representation of various types of oligonucleotide triphosphates. The use of DNA is shown, but the oligonucleotide could be RNA, DNA or a hybrid thereof.
Figure 3:
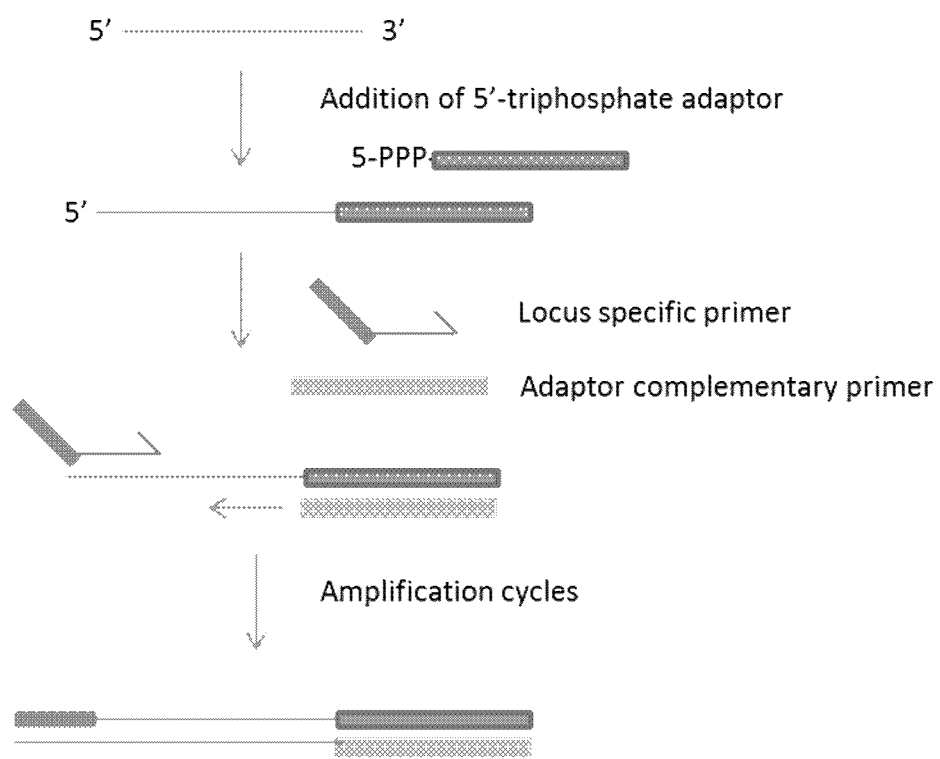
FIG. 3 shows a diagrammatic scheme for the production of a population of bi-adapted linear DNA strands using locus specific amplification.
Figure 4:
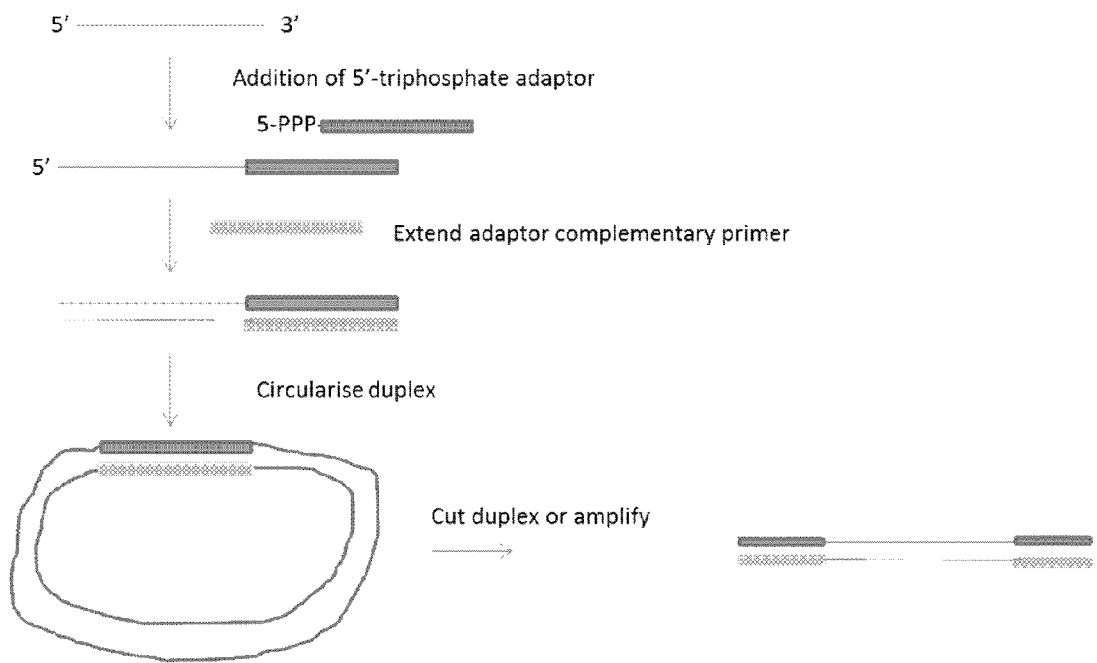
FIG. 4 shows a diagrammatic scheme for the production of a population of bi-adapted linear duplexes by strand extension, circularisation and linearisation.
Figure 5:
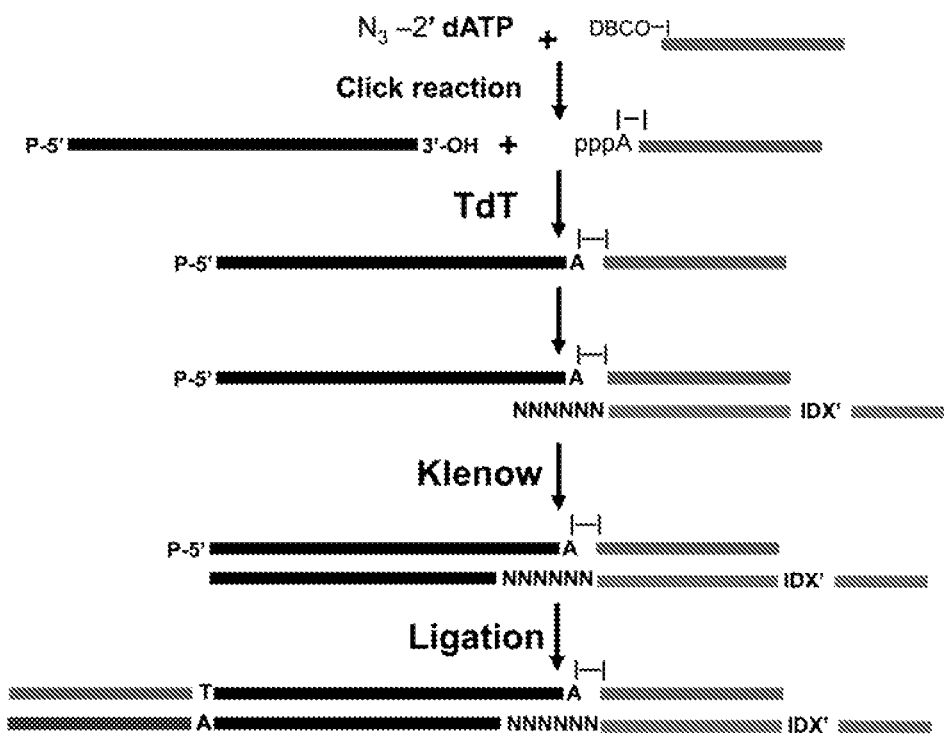

FIG. 5 shows a diagrammatic scheme for the production of a single stranded library using an oligonucleotide triphosphate. The oligonucleotide triphosphate is produced by reacting an azido dATP with an oligonucleotide containing DBCO. The oligonucleotide 5'-triphosphate can be joined to the 3'OH of a further oligonucleotide using TdT. A primer can be hybridised which bridges the first and second oligonucleotides and cross the 'un-natural' join. The primer has unspecified 'N' bases at the 3' end to hybridise to each of the different members in the library. The primer can be extended to copy the molecules from the library and produce double stranded fragments. A further adapter can be attached to the extended ends of the double stranded fragments.

Figure 6:
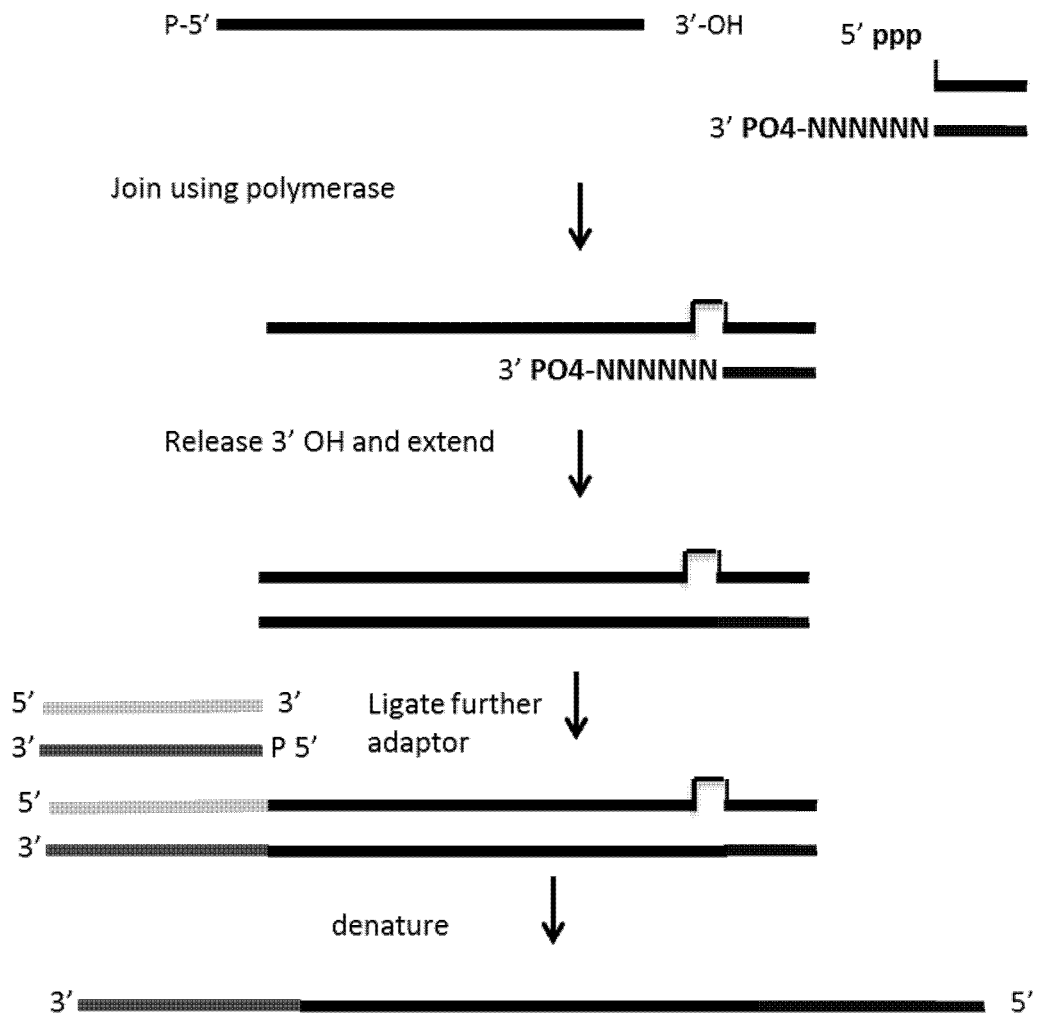

FIG. 6 shows a diagrammatic scheme for the production of a single stranded library using an oligonucleotide triphosphate adapter which is double stranded. The method includes the steps of joining two oligonucleotides using a template dependent polymerase or a template independent polymerase such as TDT, extension of the complement to the attached oligonucleotide using the 3'-end to form an extended duplex and ligation of a further adapter to the extended hairpin. Thus known regions are added to either end of a single stranded sample.

Figure 7:
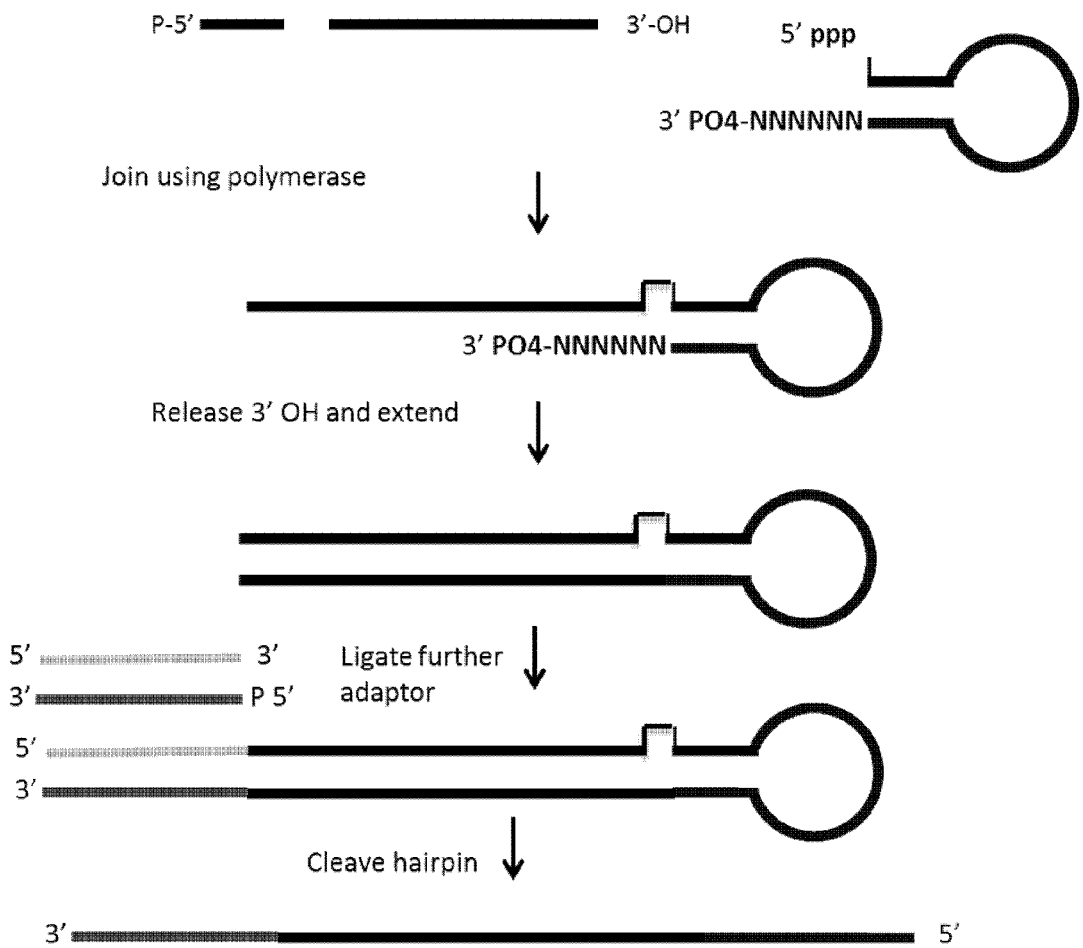

FIG. 7 shows a diagrammatic scheme for the production of a single stranded library using an oligonucleotide triphosphate having a self-complementary region (an oligonucleotide triphosphate hairpin). The method includes the steps of joining two oligonucleotides using a template dependent polymerase or a template independent polymerase such as TDT, extension of the attached oligonucleotide using the 3'-end to form an extended hairpin and ligation of a further adapter to the extended hairpin.

Figure 8:
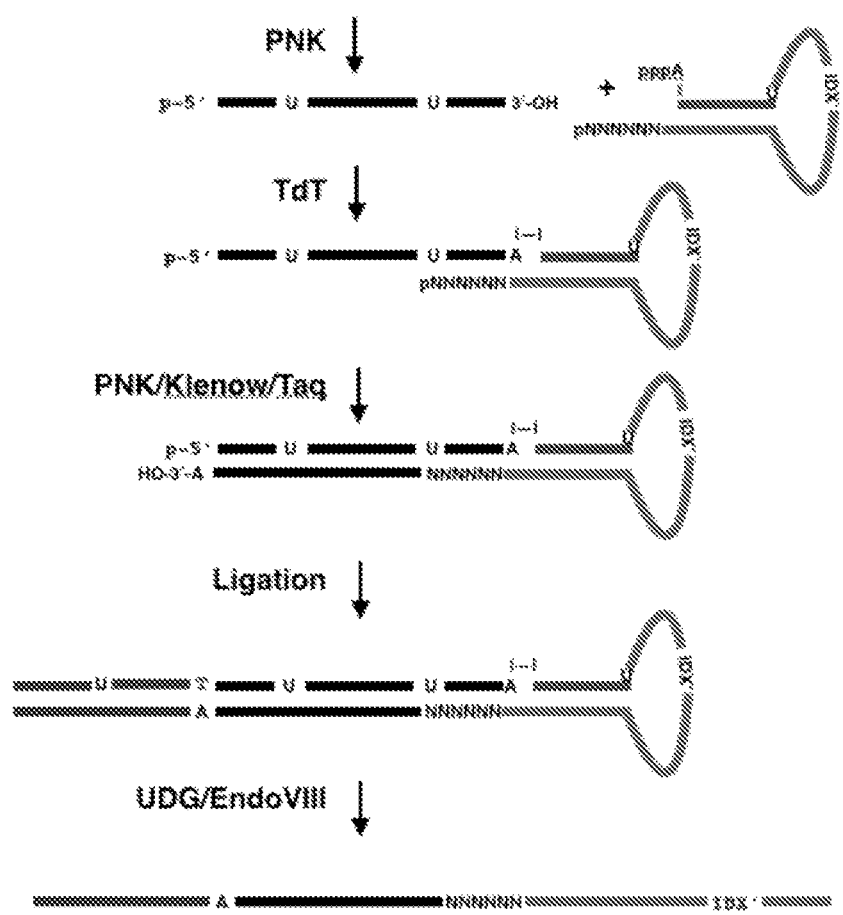

FIG. 8 shows a diagrammatic scheme for the production of a single stranded library using an oligonucleotide triphosphate having a self-complementary region (an oligonucleotide triphosphate hairpin). The method includes the steps of joining two oligonucleotides using TDT, extension of the attached oligonucleotide using the 3'-end to form an extended hairpin and ligation of a further adapter to the extended hairpin. The method shown uses a sample and an oligonucleotide triphosphate containing uracil bases, which upon digestion cleave to release a single stranded sample where both ends are known sequences.

Figure 9:
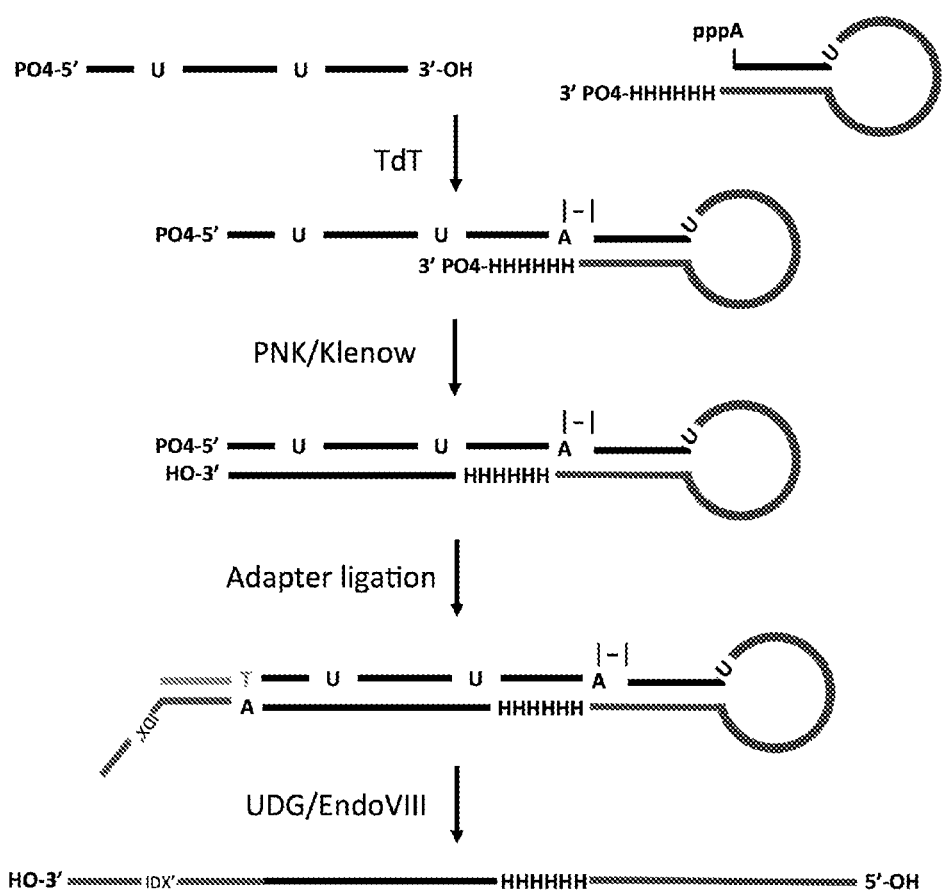

FIG. 9 shows a diagrammatic scheme for the production of a single stranded library using an oligonucleotide triphosphate having a self-complementary region (an oligonucleotide triphosphate hairpin). The hairpin has a region of bases at the 3' end marked as H (representing 'not G'). The 'H' bases hybridise to a sample treated with bisulfite, where the bases are A, T, U and G (i.e. 'not C'). The method includes the steps of joining two oligonucleotides using TDT, extension of the attached oligonucleotide using the 3'-end to form an extended hairpin and ligation of a further adapter to the extended hairpin. The method shown uses a bisulfite treated sample and an oligonucleotide triphosphate hairpin containing uracil bases, which upon digestion cleave to release a single stranded sample where both ends are known sequences. The digested single stranded sample contains the H bases internally to the known 5' and 3' ends.

Figure 10:
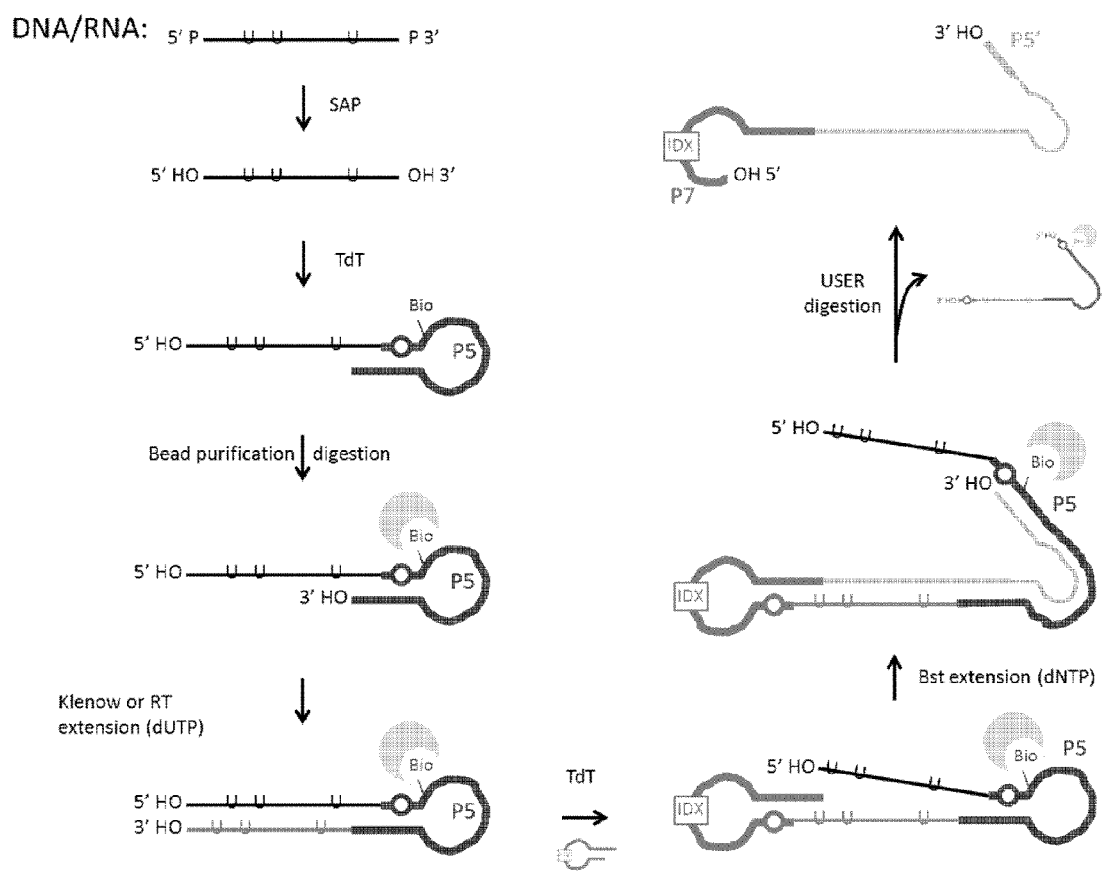

FIG. 10 shows a diagrammatic scheme for the production of a single stranded library using an oligonucleotide triphosphate having a self-complementary region (an oligonucleotide triphosphate hairpin). As with all schemes shown herein, the sample can be DNA or RNA. The sample is made into single stranded fragments averaging a few hundred base pairs in length. The adapter has a biotin group for surface attachment. The sample can be joined to the adapter in solution, or the adapter can be pre-attached to a solid support. The material attached to the solid support can undergo purification. The sample can be treated to release a 3' hydroxyl. The 3' hydroxyl of the hairpin can be extended using a suitable enzyme, for example reverse transcriptase (RT) where the sample is RNA or klenow polymerase where the sample is DNA. The extension can be carried out using dUTP. The sample can have a second hairpin adapter attached to the extended end. The second hairpin can have a free 3' hydroxyl suitable for extension. Extension of the second adapter produces a sample which extends 'back' through the first hairpin adapter. The extension may be carried out using dTTP instead of dUTP. Digestion with a uracil specific glycosylase results in cleavage of everything other than the second (dTTP) extension products. Thus producing a sample having a sequenceable region of DNA between known ends, the ends being derived from the adapter sequences.

Figure 11:
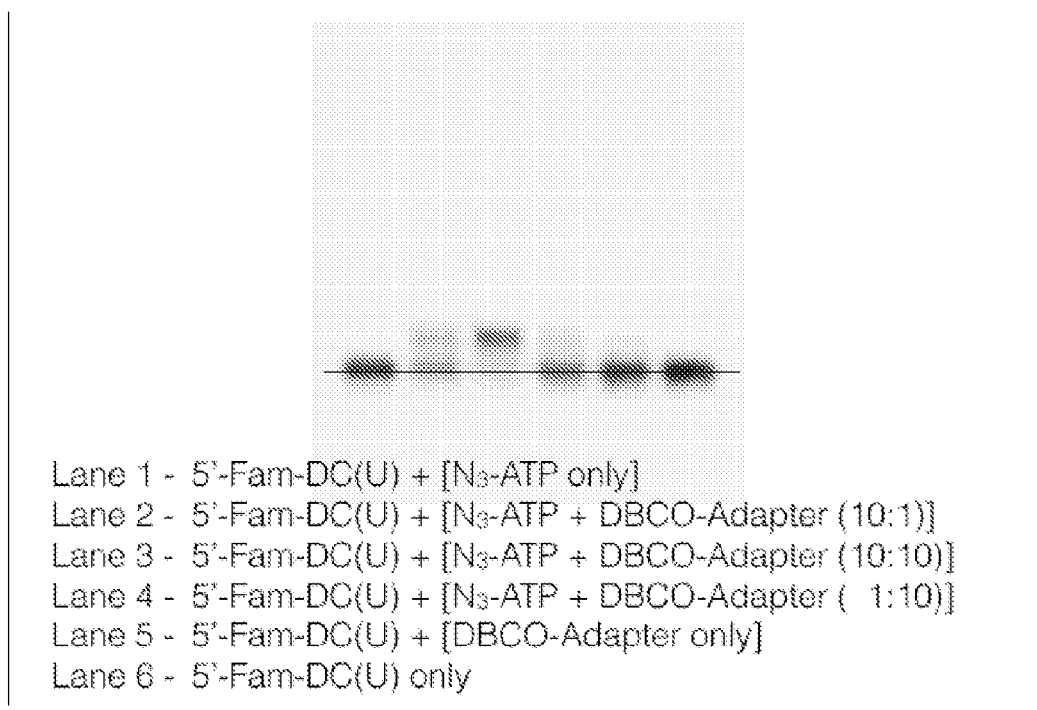

FIG. 11 shows a fluorescent gel indicating the results of joining oligonucleotides using TdT. The experimental data/gel image above shows that neither the azido modified Cordycepin triphosphate (N3-ATP) (lane 1), or the alkyne modified DNA sequence (Lane 5) is sufficient to shift the 5'Fam-DC(U) band. However, a combination of the azido modified Cordycepin triphosphate (N3-ATP) linked to a 5' alkyne modified DNA sequence (DBCO-Adapter) (Lane 2, 3 and 4) provides a band shift. This provides direct evidence that a 5' triphosphate labelled oligonucleotide can be used to directly adapt the 3' end of a single stranded oligonucleotide using a template independent polymerase. Lane 3 shows that a 10 fold excess of both the triphosphate and the adapter causes the FAM-DC(U) to be substantially all converted to the joined oligonucleotide.

FIG. 12 shows a 4-20% PAGE TBE gel of OmniPin-adapted templates (templates with a hairpin triphosphate added thereto). The bandshift observed in the gel is consistent with each hairpin-triphosphate adapter successfully adding to the 3' end of the 100mer CEG_DC_U template.

FIG. 13 shows a 2% agarose gel showing PCR-amplified libraries prepared with triphosphate-hairpins (OmniPrep libraries). The results show that both an on-bead based variant of OmniPrep and the use of dATPαS instead of dATP are possible and add performance benefits to the ssDNA library construction method. Furthermore, nuclease treatment prior to ligation can be used to reduce potential contaminants and unwanted side-products (for example, adapter-dimer) while maintaining the integrity of the sample-prepped library.

Disclosed herein is a method comprising;
a) providing a sample containing a population of nucleic acid molecules,
b) treating the population to produce a sample of DNA strands containing a mixture of first single stranded oligonucleotides of different sequence,
c) joining a second oligonucleotide sequence to the sample of DNA strands using template independent nucleic acid polymerase, and
d) producing a copy of the first single stranded oligonucleotides.

Disclosed herein is a method comprising;
a) providing a sample containing a population of nucleic acid molecules,
b) treating the population to produce a sample of DNA strands containing a mixture of first single stranded oligonucleotides of different sequence,
c) joining a second oligonucleotide sequence having a 5'-triphosphate to the sample of DNA strands, and
d) producing a copy of the first single stranded oligonucleotides.

Disclosed herein is a method of preparing a nucleic acid sample for sequencing comprising;
a) providing a sample containing a population of nucleic acid molecules,
b) treating the population to produce a sample of DNA strands containing a mixture of first single stranded oligonucleotides of different sequence,
c) joining an nucleotide triphosphate to the sample of DNA strands using a nucleic acid polymerase, wherein the nucleotide triphosphate is part of an oligonucleotide adapter which can hybridse at least in part with the sample of DNA strands; and
d) producing a complementary copy of the first single stranded oligonucleotides using the extendable 3'-end of the oligonucleotide adapter, The method may contain additional steps or features. Additional features or steps may include:

The second oligonucleotide, or oligonucleotide adapter may have a region of self-complementarity such that the second oligonucleotide may take the form of a hairpin. The hairpin, when in hybridised form, may have 3'-overhang suitable for polymerase extension. Hairpins are single oligonucleotide strands which can form intra-molecular double stranded regions. A hairpin is a nucleic acid sequence containing both a region of single stranded sequence (a loop region) and regions of self-complementary sequence such that an intra-molecular duplex can be formed under hybridising conditions (a stem region). The stem may also have a single stranded overhang. Thus the hairpin may have more than one single stranded region, the loop and the overhang. The hairpin may have 3'-overhang suitable for polymerase extension. The overhang may stretch across the triphosphate 'linker' region at the 5' end, thus avoiding any issues relating the presence of the 5'-'linker' modification required for TDT incorporation. The self-complementary double stranded portion may be from 5-20 base pairs in length. The overhang may be from 1-10 bases in length. The overhang may contain one or more degenerate bases. The sequence may contain a mixture of bases A, C and T at each position (symbolised as H (not G)). H may be used in cases where the sample is bisulfite treated, and thus does not contain any C bases to which the G would be complementary. The overhang may consist of 1-10 H bases. The overhang may be 2-8 bases, which may be H. The overhang may have a 3'-phosphate. The overhang may have a 3'-OH.

Disclosed herein is a method of joining a first single stranded oligonucleotide and an at least partly double stranded oligonucleotide adapter, wherein the first single stranded oligonucleotide is a member of a population of fragments obtained by cleaving a biological sample and the second oligonucleotide adapter has a double stranded portion and a 3'-overhang which hybridises to the first single stranded oligonucleotide, where the joining is carried out between a 3' hydroxyl of the first single stranded oligonucleotide and a 5'-triphosphate of the adapter. The adapter may consist of one or two strands (i.e. a hairpin or a duplex). The attachment may be catalysed by a template dependent or template independent polymerase.

Disclosed herein is a method of joining a first single stranded oligonucleotide and an oligonucleotide adapter using a template independent nucleic acid polymerase enzyme, wherein the first single stranded oligonucleotide is a member of a population of fragments obtained by cleaving a biological sample and the second oligonucleotide adapter takes the form of a hairpin having a single stranded region and a region of self-complementary double stranded sequence. The region of self-complementary double stranded sequence is capable of forming a duplex under hybridising conditions. Hybridising conditions may be for example 50° C. in a standard biological buffer as indicated in the experimental section below.

The second oligonucleotide may have one or more regions for indexing such that different oligonucleotides can be attached to different samples, thereby allowing sample pooling.

The second oligonucleotide, or the complement thereof where the second oligonucleotide is double stranded, is generally a chemically synthesised material having known length and modifications. The second oligonucleotide may have one or more modifications which allow site specific strand cleavage. The second oligonucleotide may have one or more uracil bases, thereby allowing site specific cleavage using enzyme treatment. The second oligonucleotide may be a hairpin and the method may include a further step of cleaving the hairpin. Cleavage of the hairpin means the two strands are no longer joined. If more than one cleavage site is present, one of the strands may be fragmented such that only one of the two strands remains intact and contains the desired properties of having two ends of known sequence. Where the adapter is double stranded, the method may include a step of denaturing the extended material.

The second oligonucleotide or the strand hybridised thereto may have one or more bases which vary in sequence at the same location (i.e. the second oligonucleotide is a member of a population of second oligonucleotides). Such bases may be represented using the universal nucleotide codings known in the art. Such universal bases may be represented as N (all four bases A, G, C and T). In order to be used with bisulfite treated samples, which are depleted in C bases, the 3 bases may be represented by H (A, T and C (i.e. 'not G'). The 3' end of the second oligonucleotide, when in the form of a hairpin, may contain a region of bases shown as 'H'.

The second oligonucleotide or the strand hybridised thereto may have one or more modifications to allow attachment to a solid support. For example the second oligonucleotide may contain biotin. Cleavage of the hairpin may allow part of the material to be eluted from the solid support in single stranded form, whilst the remaining part stays attached to the solid support.

A solid support is an insoluble, non-gelatinous body which presents a surface on which the polynucleotides can be immobilised. Examples of suitable supports include glass slides, microwells, membranes, or microbeads. The support may be in particulate or solid form, including for example a plate, a test tube, bead, a ball, filter, fabric, polymer or a membrane. Polynucleotides may, for example, be fixed to an inert polymer, a 96-well plate, other device, apparatus or material which is used in a nucleic acid sequencing or other investigative context. The immobilisation of polynucleotides to the surface of solid supports is well-known in the art. In some embodiments, the solid support itself may be immobilised. For example, microbeads may be immobilised on a second solid surface.

The copies of the first single stranded oligonucleotides may be produced by extending the 3'-end of the attached hairpin or the 3' end of the duplex where the adapter is double stranded. The extension of the hairpin produces an extended hairpin. The extended hairpin can also be described as a double stranded nucleic acid having one end joined. Upon denaturation, the extended hairpin becomes a single stranded molecule, but the length of the double stranded portion (for example at least 100 base pairs) means that the sample rapidly hybridises to form the extended hairpin.

In cases where the adapter or hairpin contains a blocking moiety at the 3' end, the blocking moiety can be removed. For example the 3' end may be a phosphate. Methods of the invention may include a step of removing the phosphate moiety, for example treatment with a suitable kinase such as polynucleotide kinase (PNK).

Attachment of the 5'-triphosphate oligonucleotide may give rise to a join which is not a natural phosphodiester linkage. Such joins may not be substrates for nucleic acid polymerases. In such cases, the use of 3'-overhangs, either as hairpins or double stranded adapters is advantageous as the linking region can be 'bridged' using an oligonucleotide primer sequence which is internal or part of the adapter. Hybridisation of a primer suitable for extension would also require such an internal spacer, and this lowers the affinity and specificity of the primer hybridisation, whereas no such issues arise where the adapter has an 'internal' primer which is already hybridised (or in the case of hairpins integral). The attachment of a single 'hairpin' which can be used as both the known end and the extendable primer when preparing a library (as shown in FIGS. 6-9) is therefore advantageous over the attachment of a single known end followed by the hybridisation of a second primer (as shown in FIG. 5). The pre-formed, or intra-molecular hybridisation spans the unnatural join, and allows efficient extension.

The extension can be carried out using a suitable enzyme and dNTP's. Where the sample is RNA, a reverse transcriptase can be used to produce the DNA/RNA duplex via the complementary DNA. Where the sample is DNA a nucleic acid polymerase can be used. The enzyme can be thermophilic or mesophilic. Suitable polymerases may include Klenow, Taq, Vent polymerase etc. If cleavage of the extended started is desired, the extension can be carried out using dUTP as a replacement for dTTP. A mixture of dUTP, dATP, dCTP and dGTP allows for complete extension as all four bases are present but allows selective strand cleavage at the uracil nucleotides. If it is desired to leave the strand intact, then dTTP case be used along with dATP, dCTP and dGTP. The nucleotide extension mix can include one or more modified dNTP's. For example the nucleotides may be used such that the resultant extended chains are not susceptible to exonuclease degradation. One or more of the dNTP's can be alpha-PS dNTPs, such that upon incorporation an exonuclease resistant thiophosphate (PS) linkage is formed.

The extended hairpin has a double stranded end. To which can be attached a further (third) oligonucleotide. Either or both strands can be adapted by the attachment of the further oligonucleotide. More commonly a double stranded adapter would be used, thereby adapting and extending both strands. The resultant product could be described as an even further extended hairpin. Methods of using hairpins are shown in FIGS. 7-9.

After addition of further adapters, the sample may be treated to remove any adapter-adapter dimers. The treatment may involve exposure to one or more nucleases. Where the extension sample contains PS linkages, the sample is protected from digestion, whilst the adapters containing no PS linkages are digested and removed.

If the original sample resulted from a bisulfate treatment step (hence containing uracil bases), it is possible to treat the sample to fragment the strand at the uracil locations. Inclusion of one or more uracil bases in the oligonucleotide triphosphate means the adapter can also be cleaved. Exposure with an enzyme mix such as UDG/EndoVIII (USER) results in the formation of fragments having no uracil bases. Thus the hairpins can be treated to be made single stranded.

Disclosed herein is a method of preparing a nucleic acid sample for sequencing comprising;
  a) providing a sample containing a population of nucleic acid molecules,
  b) treating the population to produce a sample of DNA strands containing a mixture of first single stranded oligonucleotides of different sequence,
  c) joining an nucleotide triphosphate to the sample of DNA strands using a nucleic acid polymerase, wherein the nucleotide triphosphate is part of an oligonucleotide adapter which can hybridse at least in part with the sample of DNA strands.
  d) producing a complementary copy of the first single stranded oligonucleotides using the extendable 3'-end of the oligonucleotide adapter,
  e) attaching a third oligonucleotide to the sample of DNA strands, and
  f) denaturing the products of step e; thereby producing a mixture of nucleic acid molecules where each molecule in the mixture is a copy of a molecule from the population of nucleic acid molecules and has a known region at each end.

Disclosed herein is a method of preparing a nucleic acid sample for sequencing comprising;
  a) providing a sample containing a population of nucleic acid molecules,
  b) treating the population to produce a sample of DNA strands containing a mixture of first single stranded oligonucleotides of different sequence,
  c) joining a second oligonucleotide sequence to the sample of DNA strands using template independent nucleic acid polymerase, wherein the second oligonucleotide sequence is a hairpin having an extendable 3'-end.
  d) producing a complementary copy of the first single stranded oligonucleotides using the extendable 3'-end of the hairpin,
  e) attaching a third oligonucleotide to the sample of DNA strands, and
  f) cleaving the first single stranded oligonucleotides whilst leaving the copies thereof intact; thereby producing a mixture of nucleic acid molecules where each molecule in the mixture is a copy of a molecule from the population of nucleic acid molecules and has a known region at each end.

Such methods are exemplified in FIGS. 6 to 10.

The joined fragments can be used in any subsequent method of sequence determination. For example, the fragments can undergo parallel sequencing on a solid support. In such cases the attachment of universal adapters to each end may be beneficial in the amplification of the population of fragments. Suitable sequencing methods are well known in the art, and include Illumina sequencing, pyrosequencing (for example 454 sequencing) or Ion Torrent sequencing from Life Technologies™).

Populations of nucleic acid molecules with a 3' adapter oligonucleotide and optionally a 5' second adapter oligonucleotide may be sequenced directly. For example, the sequences of the first and second adapter oligonucleotides may be specific for a sequencing platform. For example, they may be complementary to the flowcell or device on which sequencing is to be performed. This may allow the sequencing of the population of nucleic acid fragments without the need for further amplification and/or adaptation.

The first and second adapter sequences are different. Preferably, the adapter sequences are not found within the human genome.

The nucleic acid strands in the population may have the same first adapter sequence at their 3' ends and the same second adapter sequence at their 5' ends i.e. all of the fragments in the population may be flanked by the same pair of adapter sequences.

Adapting a population of single stranded nucleic acid fragments for sequencing as described herein avoids the need to produce copies or complementary strands. This is advantageous as it avoids bias introduced by amplification and other processes.

Suitable adapter oligonucleotides for the production of nucleic acid strands for sequencing may include a region that is complementary to the universal primers on the solid support (e.g. a flowcell or bead) and a region that is complementary to universal sequencing primers (i.e. which when annealed to the adapter oligonucleotide and extended allows the sequence of the nucleic acid molecule to be read). Suitable nucleotide sequences for these interactions are well known in the art and depend on the sequencing platform to be employed. Suitable sequencing platforms include Illumina TruSeq, LifeTech IonTorrent, Roche 454 and PacBio RS.

For example, the sequences of the first and second adapter oligonucleotides may comprise a sequence that hybridises to complementary primers immobilised on the solid support (e.g. a 20-30 nucleotides); a sequence that hybridises to sequencing primer (e.g. a 30-40 nucleotides) and a unique index sequence (e.g. 6-10 nucleotides). Suitable first and second adapter oligonucleotides may be 56-80 nucleotides in length.

Following adaptation and/or labelling as described herein, the nucleic acid molecules may be purified by any convenient technique. Following preparation, the population of nucleic acid molecules may be provided in a suitable form for further treatment as described herein. For example, the population of nucleic acid molecules may be in aqueous solution in the absence of buffers before treatment as described herein.

In other embodiments, populations of nucleic acid molecules with a 3' adapter oligonucleotide and optionally a 5' adapter oligonucleotide, may be further adapted and/or amplified as required, for example for a specific application or sequencing platform.

Preferably, the nucleic acid strands in the population may have the same first adapter sequence at their 3' ends and the same second adapter sequence at their 5' ends i.e. all of the fragments in the population may be flanked by the same pair of adapters, as described above. This allows the same pair of amplification primers to amplify all of the strands in the population and avoids the need for multiplex amplication reactions using complex sets of primer pairs, which are susceptible to mis-priming and the amplification of artefacts.

Suitable first and second amplification primers may be 20-25 nucleotides in length and may be designed and synthesised using standard techniques. For example, a first amplification primer may hybridise to the first adapter sequence i.e. the first amplification primer may comprise a nucleotide sequence complementary to the first adapter oligonucleotide; and a second amplification primer may hybridises to the complement of second adapter sequence i.e. the second amplification primer may comprise the nucleotide sequence of the second adapter oligonucleotide. Alternatively, a first amplification primer may hybridise to the complement of first adapter sequence i.e. the first amplification primer may comprise a nucleotide sequence of the first adapter oligonucleotide; and a second amplification primer may hybridise to the second adapter sequence i.e. the second amplification primer may comprise the nucleotide sequence of the second adapter oligonucleotide.

In some embodiments, the first and second amplification primers may incorporate additional sequences.

Additional sequences may include index sequences to allow identification of the amplification products during multiplex sequencing, or further adapter sequences to allow sequencing of the strands using a specific sequencing platform.

EXPERIMENTS

All reagents and buffers are commercially available unless otherwise stated.

Example 1

Preparation of Oligonucleotide Triphosphates

Shown below is the ligation of the azido modified Cordycepin triphosphate (N3-ATP) to a 5' alkyne modified DNA sequence (DBCO-Adapter) using copper-free click chemistry. The click reaction forms the 5' triphosphate modified oligonucleotide (ATP-Triazole-Adapter). The 5' triphosphate modified oligonucleotide (ATP-Triazole-Adapter) is then ligated to the 3' end a second oligonucleotide (5'Fam-DC(U)) in a non templated fashion using TdT.

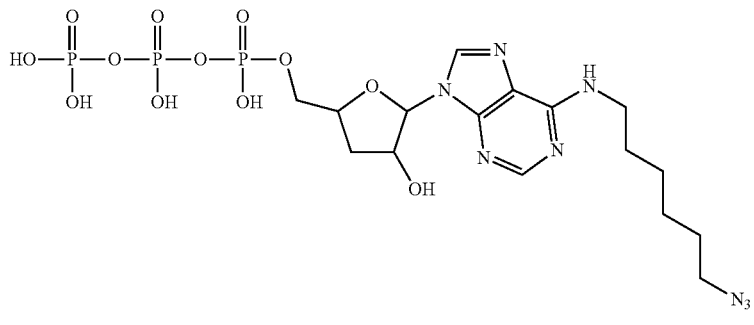

N3-ATP

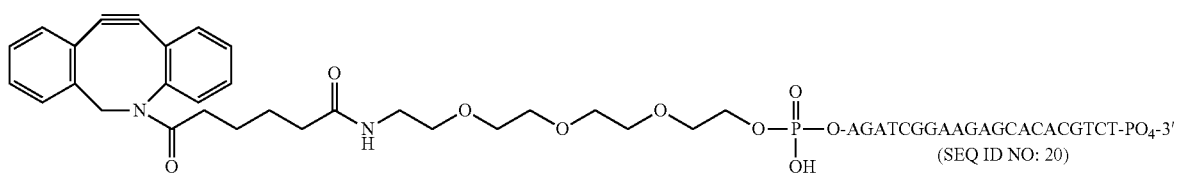

DBCO-Adapter (SEQ ID NO: 20)

-continued

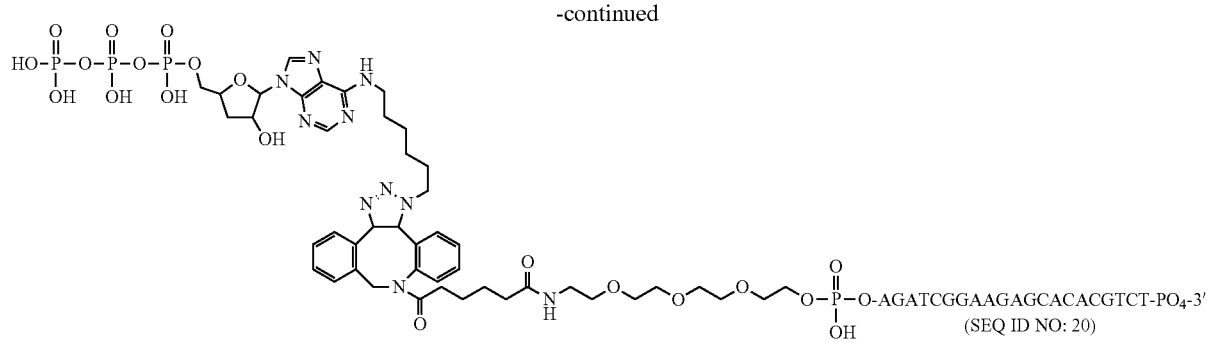

ATP-Triazole-Adaptor

5'-FAM-DC(U)
5'-FAM-CTCACCCACAACCACAAACATACGATCACGGCGAATCCGATCGAATCAGTTCCGCGCTTTAUGAAGTGCGACAGCCTTAGTGATGTGATGGGTGGTATGG-OH-3'
(SEQ ID NO: 1)

Reaction Conditions.

To 2 µL of DBCO-Adapter DNA (500 mM in DMSO) was added 2 µL of N3-ATP (500 mM in water) and incubated at 37° C. for 1 hr. To the ligated ATP-Triazole-Adapter was added 2 µL, of TdT buffer (10×), 2 µL of CoCl2 (10×) and 5 µL of 5'-FAM-DC(U) DNA, the reaction was made unto 20 µL with water and incubated at 37° C. for 30 mins. The reaction mixture was loaded directly onto a 4% agarose gel using 4 µL of a 6× loading buffer, and run for 3 hr at 90V. The gel was imaged using a Typhoon imager using the standard setting for detecting the Fam flurophore (FIG. 11).

The experimental data/gel image (FIG. 11) shows that neither the azido modified Cordycepin triphosphate (N3-ATP) (lane 1), or the alkyne modified DNA sequence (Lane 5) is not sufficient to shift the 5'Fam-DC(U) band. However, a combination of the azido modified Cordycepin triphosphate (N3-ATP) linked to a 5' Alkyne modified DNA sequence (DBCO-Adapter) is (Lane 2, 3 and 4) provides a band shift. This provides direct evidence that a 5' triphosphate labelled oligonulceotide can be used to directly adapt the 3' end of a single stranded oligonucleotide using a template independent polymerase. Lane 3 shows that a 10 fold excess of both the triphosphate and the adapter causes the FAM-DC(U) to be substantially all converted to the joined oligonucleotide.

Example 2

Addition of a Hairpin-triphosphate Adapter to ssDNA

Materials:
Oligonucleotides used in the experiment are listed in Table 1.

TABLE 1

| Oligonucleotide sequences | |
|---|---|
| Oligonucleotide | Sequence 5'-3' |
| CEG_DC_U | pCTCACCCACAACCACAAACATAUGATUAUGGUGAAUUUGAUUGAAUUAGTTUUGUGUTTTAUGAAGTGUGAUAGUUTTAGTGATGTGATGGGTGGTATNN (SEQ ID NO: 2) |

TABLE 1-continued

| Oligonucleotide sequences | |
|---|---|
| Oligonucleotide | Sequence 5'-3' |
| CEG_OP_6H_IDX_1 | DBCO-GATCGGAAGAGCTCAAGCAGAAGACGGCATACGAGAT<u>CGTGAT</u>GTGACTGGAGTTCAGACGTGTGCTCTTCCGATCTHHHHHHp (SEQ ID NO: 3) |
| CEG_OP_6H_IDX_4 | DBCO-GATCGGAAGAGCTCAAGCAGAAGACGGCATACGAGAT<u>TGGTCA</u>GTGACTGGAGTTCAGACGTGTGCTCTTCCGATCTHHHHHHp (SEQ ID NO: 4) |
| CEG_OP_6H_IDX_5 | DBCO-GATCGGAAGAGCTCAAGCAGAAGACGGCATACGAGAT<u>CACTGT</u>GTGACTGGAGTTCAGACGTGTGCTCTTCCGATCTHHHHHHp (SEQ ID NO: 5) |
| CEG_OP_6H_IDX_6 | DBCO-GATCGGAAGAGCTCAAGCAGAAGACGGCATACGAGAT<u>ATTGGC</u>GTGACTGGAGTTCAGACGTGTGCTCTTCCGATCTHHHHHHp (SEQ ID NO: 6) |
| CEG_OP_6H_IDX_2 | DBCO-GATCGGAAGAGCTCAAGCAGAAGACGGCATACGAGAT<u>ACATCG</u>GTGACTGGAGTTCAGACGTGTGCTCTTCCGATCTHHHHHHp (SEQ ID NO: 7) |
| CEG_OP_6H_IDX_3 | DBCO-GATCGGAAGAGCTCAAGCAGAAGACGGCATACGAGAT<u>GCCTAA</u>GTGACTGGAGTTCAGACGTGTGCTCTTCCGATCTHHHHHHp (SEQ ID NO: 8) |
| CEG_OP_6H_IDX_12 | DBCO-GATCGGAAGAGCTCAAGCAGAAGACGGCATACGAGAT<u>TACAAG</u>GTGACTGGAGTTCAGACGTGTGCTCTTCCGATCTHHHHHHp (SEQ ID NO: 9) |
| CEG_OP_6H_IDX 19: | DBCO-GATCGGAAGAGCTCAAGCAGAAGACGGCATACGAGAT<u>TTTCAC</u>GTGACTGGAGTTCAGACGTGTGCTCTTCCGATCTHHHHHHp (SEQ ID NO: 10) |

DBCO = dibenzocyclooctyne
p = phosphate

Modified nucleotide triphosphates used in the experiment are listed in Table 2.

TABLE 2

Nucleotide triphosphates

| Nucleotide triphosphate | Structure |
|---|---|
| $N^6$-(6-Azido)hexyl-2'-dATP (2' dATP-N3, Jena Biosciences P/N NU-1707S) | 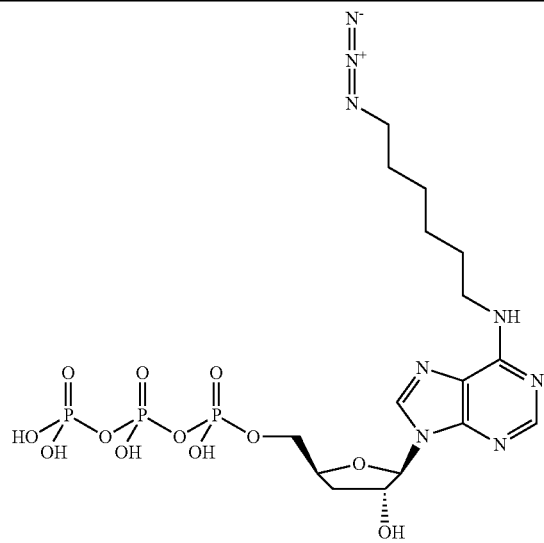 Structural formula of $N^6$-(6-Azido)hexyl-3'-dATP |

Enzymes used in the experiment are listed below.
Terminal deoxytransferase (TdT, Enzymatics P/N P7070L).

Method:

Step 1. Formation of Hairpin-triphosphate Adapters

To 0.5 μL of Tris-HCl (100 mM, pH 7.0) was added 1 nmol of 2'dATP (2 μL of 500 μM in 10 mM Tris-HCl, pH 7.0) and 1.25 nmol of the CEG_OP_6H_N adapter (2.5 μL in 500 μM in DMSO) as shown in Table 3. The mixture was incubated at 10° C. for 2 hr and diluted down to a final concentration of 100 μM by the addition of 5 μL of Tris-HCl (100 mM, pH 7.0).

TABLE 3

Hairpin-triphosphate mixes

| Ref | Volume (μL) of Tris-HCl (100 mM, pH 7.0) | Volume (μL) of $N^6$-(6-Azido)hexyl-2'-dATP (500 μM) | Volume of CEG_OP_6H_N (500 μM) |
|---|---|---|---|
| CEG19_105_1 | 0.5 | 2.0 | 2.5 (N = IDX 1) |
| CEG19_105_2 | 0.5 | 2.0 | 2.5 (N = IDX 4) |
| CEG19_105_3 | 0.5 | 2.0 | 2.5 (N = IDX 5) |
| CEG19_105_4 | 0.5 | 2.0 | 2.5 (N = IDX 6) |
| CEG19_105_5 | 0.5 | 2.0 | 2.5 (N = IDX 2) |
| CEG19_105_6 | 0.5 | 2.0 | 2.5 (N = IDX 3) |
| CEG19_105_7 | 0.5 | 2.0 | 2.5 (N = IDX 12) |
| CEG19_105_8 | 0.5 | 2.0 | 2.5 (N = IDX 19) |

Exemplary Hairpin-triphosphate Structure (e.g. CEG19_105_5)

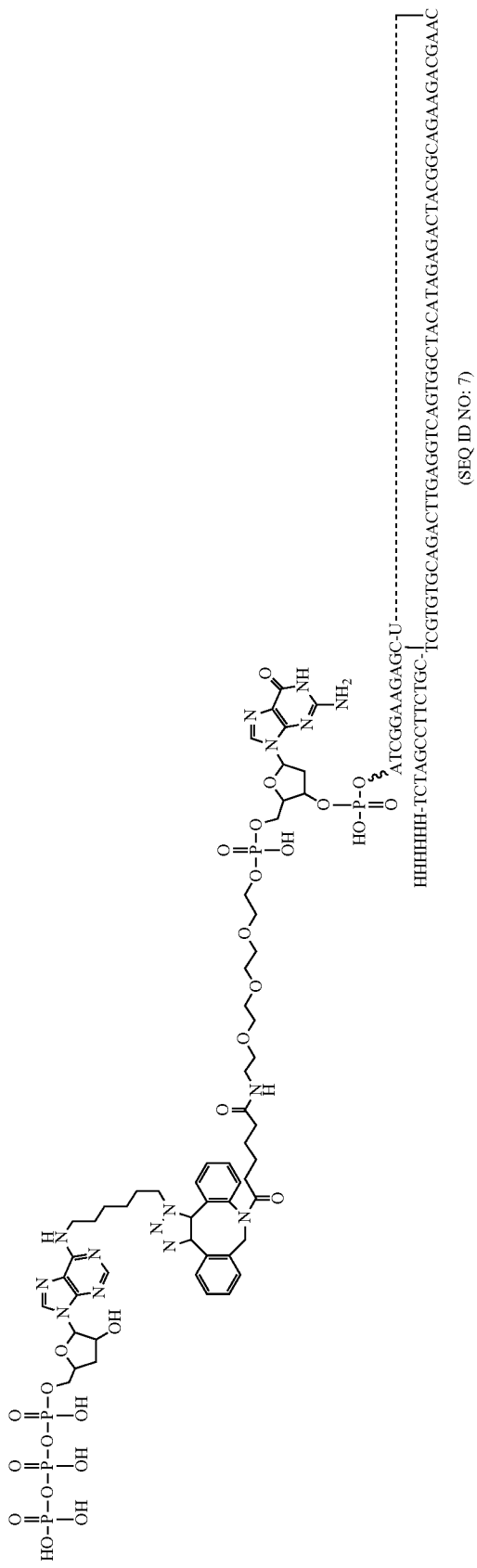

Step 2. Addition of ssDNA Template with OmniPin Adapter

To 3 pmol of ssDNA template (100 ng, CEG_DC_U) in 7 µL water was added 1 µL of CEG TdT 10× Buffer (1 M Tris-acetate, 12.5 mM cobalt acetate, 1.25 mg/mL BSA, pH 6.6), 300 pmol of the OmniPin adapter (1 uL of CEG19_105_1-8, Table 4) followed by 20 U of TdT (20 U/µL). The reaction mixture was incubated at 37° C. for 30 mins before purification of the DNA.

TABLE 4

Adaption mixes

| Ref | Volume (µL) of CEG_DC_U (100 ng/µL) | Volume (µL) dH₂O | Volume (µL) CEG TdT Buffer (10×) | Volume (µL) CEG19_100_1-8 (100 µM) | Volume (µL) TdT (10 U/µL) |
|---|---|---|---|---|---|
| CEG19_105_9 | 1 | 6 | 1 | 1 (CEG19_105_1) | 1 |
| CEG19_105_10 | 1 | 6 | 1 | 1 (CEG19_105_2) | 1 |
| CEG19_105_11 | 1 | 6 | 1 | 1 (CEG19_105_3) | 1 |
| CEG19_105_12 | 1 | 6 | 1 | 1 (CEG19_105_4) | 1 |
| CEG19_105_13 | 1 | 6 | 1 | 1 (CEG19_105_5) | 1 |
| CEG19_105_14 | 1 | 6 | 1 | 1 (CEG19_105_6) | 1 |
| CEG19_105_15 | 1 | 6 | 1 | 1 (CEG19_105_7) | 1 |
| CEG19_105_16 | 1 | 6 | 1 | 1 (CEG19_105_8) | 1 |

Results:

Purified hairpin-adapted template products (9 uL each of CEG19_105_9-16) were loaded onto a 4-20% PAGE TBE gel (Life Technologies, P/N EC62255BOX) and ran for 35 minutes at 200 V (FIG. 12). The bandshift observed in the gel is consistent with each hairpin-triphosphate adapter successfully adding to the 3' end of the 100 mer CEG_DC_U template.

Example 3

Whole Human Genome Sequencing Using Libraries Prepared with OmniPrep Single Stranded Library Construction Method Materials:

Oligonucleotides used in the experiment are listed in Table 5.

TABLE 5

Oligonucleotide sequences

| Oligonucleotide | Sequence 5'-3' |
|---|---|
| CEG_OP_6H_IDX_1 | DBCO-GATCGGAAGAGCUCAAGCAGAAGACGG CATACGAGATCGTGATGTGACTGGAGTTCAGA CGTGTGCTCTTCCGATCTHHHHHHp (SEQ ID NO: 3) |
| CEG_OP_6H_IDX_4 | DBCO-GATCGGAAGAGCUCAAGCAGAAGACGG CATACGAGATTGGTCAGTGACTGGAGTTCAGA CGTGTGCTCTTCCGATCTHHHHHHp (SEQ ID NO: 4) |
| CEG_OP_6H_IDX_5 | DBCO-GATCGGAAGAGCUCAAGCAGAAGACGG CATACGAGATCACTGTGTGACTGGAGTTCAGA CGTGTGCTCTTCCGATCTHHHHHHp (SEQ ID NO: 5) |
| CEG_OP_6H_IDX_6 | DBCO-GATCGGAAGAGCUCAAGCAGAAGACGG CATACGAGATATTGGCGTGACTGGAGTTCAGA CGTGTGCTCTTCCGATCTHHHHHHp (SEQ ID NO: 6) |
| CEG_OP_6H_IDX_2 | DBCO-GATCGGAAGAGCUCAAGCAGAAGACGG CATACGAGATACATCGGTGACTGGAGTTCAGA CGTGTGCTCTTCCGATCTHHHHHHp (SEQ ID NO: 7) |
| CEG_OP_6H_IDX_3 | DBCO-GATCGGAAGAGCUCAAGCAGAAGACGG CATACGAGATGCCTAAGTGACTGGAGTTCAGA CGTGTGCTCTTCCGATCTHHHHHHp (SEQ ID NO: 8) |
| CEG_OP_6H_IDX_12 | DBCO-GATCGGAAGAGCUCAAGCAGAAGACGG CATACGAGATTACAAGGTGACTGGAGTTCAGA CGTGTGCTCTTCCGATCTHHHHHHp (SEQ ID NO: 9) |
| CEG_OP_6H_IDX_19 | DBCO-GATCGGAAGAGCUCAAGCAGAAGACGG CATACGAGATTTTCACGTGACTGGAGTTCAGA CGTGTGCTCTTCCGATCTHHHHHHp (SEQ ID NO: 10) |
| CEG_Frw_AD_U | AATGATACGGCGACCACCGAGATCTACACTCT UTCCCTACACGACGCTCTUCCGATCT (SEQ ID NO: 11) |
| CEG_Frw_AD_Comp | pGATCGGAAGAGCGTCGTGTAGGGAAAGAGTG TAGATCTCGGTGGTCGCCGTATCATTp (SEQ ID NO: 12) |

TABLE 5-continued

Oligonucleotide sequences

| Oligonucleotide | Sequence 5'-3' |
|---|---|
| Fwd_PCR_Primer | AATGATACGGCGACCACCGAG (SEQ ID NO: 13) |
| Rev_PCR_Primer | CAAGCAGAAGACGGCATACGA (SEQ ID NO: 14) |

DBCO = dibenzocyclooctyne
p = phosphate

Modified nucleotide triphosphates used in the experiment are listed in Table 6.

TABLE 6

Nucleotide triphosphates

| Nucleotide triphosphate | Structure |
|---|---|
| $N^6$-(6-Azido)hexyl-2'-dATP (2' dATP-N3, Jena Biosciences P/N NU-1707S) | [chemical structure] |

Structural formula of $N^6$-(6-Azido)hexyl-3'-dATP

Enzymes used in the experiment are listed in Table 7 below.

TABLE 7

Enzymes

| Enzyme | Vendor and P/N |
|---|---|
| Terminal deoxytransferase (TdT) | Enzymatics P7070L |
| T4 Polynucleotide Kinase (PNK) | Enzymatics Y9040L |
| Klenow(exo-) DNA polymerase | Enzymatics P7010-HC-L |
| T4 DNA Ligase | Enzymatics L6030-HC-L |
| Thermolabile UDG | Enzymatics G5020L |
| VERASEQ™ ULtra DNA polymerase | Enzymatics P7520L |

Methods

Step 1. Formation of Hairpin-triphosphate Adapters

To 0.5 µL of Tris-HCl (100 mM, pH 7.0) was added 1 nmol of 2'dATP (2 µL of 500 µM in 10 mM Tris-HCl, pH 7.0) and 1.25 nmol of the CEG_OP_6H_* adapter (2.5 µL in 500 µM in DMSO, * denotes separate indexed hairpin adapters each listed in Table 5). Each mixture was incubated at 10° C. for 2 hr and diluted down to a final concentration of 100 µM by the addition of 5 µL of Tris-HCl (100 mM, pH 7.0).

Step 2. Bisulfite Conversion of Human Genomic DNA

Human Cerebellum genomic DNA (AMSbio, 1 µg) was bisulfite (BS) or oxidative bisulfite (oxBS) converted using the TRUEMETHYL™ conversion kit (CEGX) following the manufacturers specification. The DNA was then quantified by QUBIT™ ssDNA assay kit (Invitrogen).

Step 3. PNK Treatment of Genomic DNA

To 100 ng of either native, BS or oxBS treated human cerebellum gDNA in 1× TdT buffer (100 mM Tris-acetate, 1.25 mM $CoAc_2$, 125 µg/mL BSA, pH 6.6 @ 25° C.) supplemented with 10 Units of PNK was added and incubated at 37° C. for 20 min. The PNK reaction was stopped by heat denaturating at 95° C. for 3 min.

Step 4. Addition of the Hairpin Adapter to the PNK Treated Genomic DNA

To the PNK treated DNA (after heat denaturation) 50 pmols of the Hairpin adapter (hairpin-triphosphate adapter from step 1) and 20 Units of TdT was added and incubated at 37° C. for 30 min.

Step 4. Magnetic Bead Purification of Hairpin-adapted Genomic DNA

The hairpin-adapted DNA fragments were purified using magnetic beads (30% PEG-8000, 1 M NaCl, 1 mM EDTA, 10 mM Tris pH 8, 0.1% w/v carboxy Sera-Mag magnetic particles (GE P/N 09-981-123)). Samples were washed using freshly prepared acetonitrile:water (70:30) and eluted from the beads in ultra pure water.

Step 5. Klenow Extension and Ligation of the Second Adapter

The purified hairpin-adapted DNA fragments in 1× ligation buffer (50 mM Tris-HCl, 10 mM $MgCl_2$, 5 mM DTT, 1 mM ATP, pH 7.6 @ 25° C.) supplemented with 1 mM dNTP, 10 U of PNK and 50 U of Klenow(exo-), were incubated at 37° C. for 30 min before the PNK and Klenow(exo-) were heat denatured at 95° C. for 3 min. The reaction mixture was used directly within the ligation reaction by the addition of PEG 6000 to a final concentration of 7.5%, 0.1 pMols of pre-annealed DNA adapters and 600 U of T4 DNA Ligase. The mixture was incubated for 15 mins at 25° C. to yield the doubly-adapted DNA fragment product.

Step 6. Magnetic Bead Purification Doubly-adapted DNA Fragments

The doubly-adapted DNA fragments were purified twice with a 18% PEG solution (18% PEG-8000, 1 M NaCl, 1 mM EDTA, 10 mM Tris pH 8, 0.1% w/v Carboxy-coated magnetic particles). Samples were washed using freshly prepared acetonitrile:water (70:30) and eluted from the beads in ultra pure water.

Step 7. UDG Digestion to Yield Final Libraries

The purified doubly-adapted DNA fragments in 1× VERASEQ™ buffer were treated with 1 U of thermolibale UDG for 20 mins at 37° C. before the UDG was heat denatured at 95° C. for 5 min. This final library of single stranded, doubly adapted fragments is referred to as an OmniPrep library. Samples were either sequenced directly as PCR-free libraries or PCR-amplified for 10 cycles before sequencing.

Step 8. PCR Amplification of Omniprep Libraries

PCR amplification of the OmniPrep libraries was performed on Agilent Surecycler 8800 thermocycler in 1× VERASEQ™ buffer supplemented with 125 μM of the forward PCR primer (Fwd_PCR_Primer), 125 μM of the reverse PCR primer (Rev_PCR_Primer), 500 μM dNTPs and 1 U of VERASEQ™ 2.0 DNA polymerase. Thermocycling conditions were 10 cycles of:

Denaturation at 95° C. for 30 sec

Annealing at 60° C. for 30 sec

Extension at 72° C. for 90 sec

Step 9. Magnetic Bead Purification of Amplified Omni-Prep Libraries

The amplified OmniPrep libraries were purified once with a 18% PEG solution (18% PEG-8000, 1 M NaCl, 1 mM EDTA, 10 mM Tris pH 8, 0.1% w/v Carboxy-coated magnetic particles). Samples were washed using freshly prepared acetonitrile:water (70:30) and eluted from the beads in ultra pure water.

Step 10. Sequencing and Analysis of the OmniPrep Libraries

Sequencing was carried out on an Illumina NextSeq500 sequencer with a paired end run (2×75 bp). Two individual runs were conducted, one for the PCR-free libraries, a second for the PCR-amplified libraries. Libraries were prepared in duplicate (native) or triplicate (converted) and pooled to a final concentration of 2 nM, then denatured and diluted according to the manufacturers instructions before Sequencing. The raw output fastq read sequences were quality filtered and trimmed using TrimGalore, the trimmed data was aligned to the human genome (release 37.55) with Bismark software. A summary of the sequencing results is shown in Table 8.

TABLE 8

Whole human genome OmniPrep library sequencing metrics

| Sample | # PE reads | # uniquely mapped reads | # non-uniquely mapped reads | Alignment rate |
| --- | --- | --- | --- | --- |
| PCR_native_rep1 | 16640651 | 11507328 | 457049 | 69.2% |
| PCR_native_rep2 | 14304479 | 10632055 | 441680 | 74.3% |
| PCR_BS_rep1 | 28416019 | 17265923 | 984970 | 60.8% |
| PCR_BS_rep2 | 7866065 | 5547305 | 304164 | 70.5% |
| PCR_BS_rep3 | 32336222 | 22677644 | 1146295 | 70.2% |
| PCR_oxBS_rep1 | 35661755 | 24297095 | 1246204 | 68.2% |
| PCR_oxBS_rep2 | 24124304 | 17101247 | 990627 | 70.9% |
| PCR_oxBS_rep3 | 31384442 | 22721639 | 1186467 | 72.4% |
| PCRfree_native_rep1 | 41729358 | 32452776 | 1516459 | 77.8% |
| PCRfree_native_rep2 | 46284959 | 34231016 | 1673857 | 74.0% |
| PCRfree_BS_rep1 | 3996331 | 2282322 | 148326 | 57.1% |
| PCRfree_BS_rep2 | 7140997 | 4731152 | 300306 | 66.3% |
| PCRfree_BS_rep3 | 6164831 | 4115330 | 258993 | 66.8% |
| PCRfree_oxBS_rep1 | 20869094 | 13311899 | 863129 | 63.8% |
| PCRfree_oxBS_rep2 | 3776160 | 2469895 | 166376 | 65.5% |
| PCRfree_oxBS_rep3 | 11869124 | 8218475 | 508641 | 69.3% |

Results and Observations

The sequencing data clearly demonstrates the successful sequencing of PCR-amplified and PCR-free OmniPrep libraries prepared using ssDNA from native and converted (bisulfite and oxidative-bisulfite) human cerebellum gDNA. High alignment rates indicate that the majority of the data is comprised of unique reads that align unambiguously to the human genome. This experiment illustrates that the Omni-Prep method can be used to prepare sequencable libraries from ssDNA that accurately map to the expected genome of interest.

Example 4

On-bead OmniPrep Library Preparation

Materials

Oligonucleotides used in the experiment are listed in Table 9.

TABLE 9

| Oligonucleotide | Sequence 5'-3' |
| --- | --- |
| CEG_OPS_6H_Biotin | DBCO-GAT(Biotin)CGGAAGAGCU TACACTCTTTCCCTACACGACGCTCT TCCGATCTHHHHHHp (SEQ ID NO: 15) |
| CEG_SHORT_IDX_AD_3P | GTGACTGGAGTUCAGACGTGTGCTCT CUCGATCTp (SEQ ID NO: 16) |
| CEG_SHORT_IDX_COMP_53P | pGATCGGAAGAGCACACGTCTGAACT CCAGTCACp (SEQ ID NO: 17) |
| Fwd_PCR_Primer_long | AATGATACGGCGACCACCGAGATCTA CACTCTTTCCCTACACGACGCTCTTC CGATCT (SEQ ID NO: 18) |
| Rev_PCR_Primer_long | CAAGCAGAAGACGGCATACGAGATCA CTGTGTGACTGGAGTTCAGACGTGT (SEQ ID NO: 19) |

DBCO = dibenzocyclooctyne
p = phosphate

Modified nucleotide triphosphates used in the experiment are listed in Table 10.

TABLE 10

Nucleotide triphosphates

| Nucleotide triphosphate | Structure |
|---|---|
| $N^6$-(6-Azido)hexyl-2'-dATP (2' dATP-N3, Jena Biosciences P/N NU-1707S) | 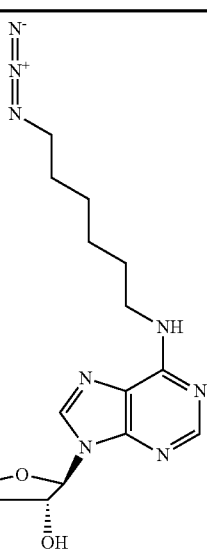<br>Structural formula of $N^6$-(6-Azido)hexyl-3'-dATP |
| 2'-Deoxyadenosine-5'-(α-thio)-triphosphate (dATPαS, Jena Biosciences NU-426S) | 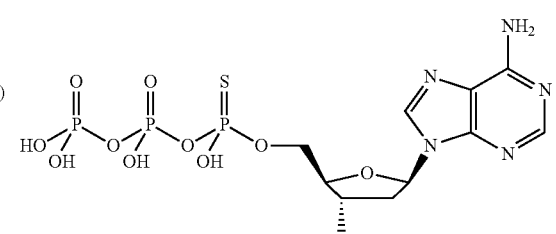 |

Enzymes used in the experiment are listed in Table 11 below.

TABLE 11

Enzymes

| Enzyme | Vendor and P/N |
|---|---|
| Terminal deoxytransferase (TdT) | Enzymatics P7070L |
| T4 Polynucleotide Kinase (PNK) | Enzymatics Y9040L |
| Klenow(exo-) DNA polymerase | Enzymatics P7010-HC-L |
| T4 DNA Ligase | Enzymatics L6030-HC-L |
| Thermolabile UDG | Enzymatics G5020L |
| VERASEQ ™ ULtra DNA polymerase | Enzymatics P7520L |
| Exonuclease 1 (ExoI) | Enzymatics X8010L |
| Exonuclease VII (ExoVII) | NEB M0379S |
| Exonuclease T (ExoT) | NEB M0265S |
| Endonuclease VII (EndoVII) | Enzymatics Y9080L |

Method

Step 1. Formation of Hairpin-triphosphate (OmniPin) Adapters

To 0.5 µL of Tris-HCl (100 mM, pH 7.0) was added 1 nmol of 2'dATP (2 µL of 500 µM in 10 mM Tris-HCl, pH 7.0) and 1.25 nmol of the CEG_OPS_6H_Biotin adapter (2.5 µL in 500 µM in DMSO). Each mixture was incubated at 10° C. for 2 hr and diluted down to a final concentration of 100 µM by the addition of 5 µL of Tris-HCl (100 mM, pH 7.0).

Step 2. Bisulfite Conversion of Human Genomic DNA

Human genomic DNA (Promega, 1 µg) was bisulfite (BS) converted using the TRUEMETHYL™ conversion kit (CEGX) following the manufacturers specification. The DNA was then quantified by QUBIT™ ssDNA assay kit (Invitrogen).

Step 3. PNK Treatment of Genomic DNA

To 60 ng of BS converted DNA in 1× TdT buffer (100 mM Tris-acetate, 1.25 mM CoAc$_2$, 125 µg/mL BSA, pH 6.6 @ 25° C.) 10 U of PNK was added and incubated at 37° C. for 20 min. The PNK reaction was stopped by denaturating at 95° C. for 3 min.

Step 4. Addition of the Hairpin-triphosphate Adapter to the PNK Treated Genomic DNA To the PNK treated DNA after heat denaturation 50 pmols of the OmniPin adapter (hairpin-triphosphate adapter) and 20 U of TdT was added and incubated at 37° C. for 30 min.

Step 5. Binding of OmniPin-adapted DNA Fragments to Streptavidin Coated Magnetic Beads The OmniPin-adapted DNA fragments were bound to 50 µL of streptavidin coated magnetic particles (Life Technologies Dynabeads, M280) in 1× BW buffer (1 M NaCl, 5 mM Tris-HCl, 0.5 mM EDTA, 0.1% Tween, pH 8.0 at 25° C.) for 30 mins at 25° C.

Step 6. Washing of Immobilised OmniPin-adapted DNA Fragments

DNA-bound streptavidin coated magnetic particles were precipitated on a magnetic rack and the supernatant was removed and discarded. The beads were washed twice, by re-suspending in a high stringency wash buffer (0.1×SSC, 0.1×SDS). The beads were finally washed with 1× Ligation buffer (50 mM Tris-HCl, 10 mM $MgCl_2$, 5 mM DTT, 1 mM ATP, pH 7.6 @ 25° C.).

Step 7. On-bead Klenow Extension of OmniPin-adapted DNA Fragments

The washed DNA-bound streptavidin beads were re-suspended in 1× ligation buffer (50 mM Tris-HCl, 10 mM $MgCl_2$, 5 mM DTT, 1 mM ATP, pH 7.6 @ 25° C.) supplemented with 0.25 mM dNTP (dATPαS was used in place of dATP), 10 U of PNK and 50 U of Klenow(exo-). The reaction was incubated at 37° C. for 30 min.

Step 8. Washing of Klenow Extended Immobilised OmniPin-adapted DNA Fragments

Extended DNA-bound streptavidin coated magnetic particles were precipitated on a magnetic rack and the supernatant was removed. The beads were washed twice, by re-suspending in a high stringency wash buffer (0.1×SSC, 0.1×SDS). The beads were finally washed with 1× NEBuffer 4 (50 mM Potassium Acetate, 20 mM Tris-acetate, 10 mM Magnesium Acetate, 1 mM DTT, pH 7.9 at 25° C.).

Step 9. On-bead Nuclease Digestion of Immobilized DNA Fragments

A selection of nucleases were independently tested at this stage. The washed, Klenow extended, DNA-bound streptavidin beads were resuspended in 1× NEBuffer4 supplemented with either 10 U of Exo I, or 10 U of Exo VII, or 10 U of Exo T, or 20 U of a combination of Exo I, Exo VII and Exo T. The reactions were incubated at 37° C. for 60 min.

Step 10. Washing of Nuclease Digested Immobilised OmniPin-adapted DNA Fragments

Nuclease digested DNA-bound streptavidin coated magnetic particles were precipitated on a magnetic rack and the supernatant was removed. The beads were washed twice, by re-suspending in a high stringency wash buffer (0.1×SSC, 0.1×SDS). The beads were finally washed with 1× Ligation buffer (50 mM Tris-HCl, 10 mM $MgCl_2$, 5 mM DTT, 1 mM ATP, pH 7.6 @ 25° C.).

Step 11. On-bead Ligation of the Second Adapter

The washed nuclease-digested DNA-immobilized streptavidin beads were re-suspended in 1× Ligation buffer supplemented with 0.1 pmol of pre-annealed DNA adapters (equimolar mix of CEG_SHORT_IDX_AD_3P and CEG_SHORT_IDX_COMP_53P) and 600 U of T4 DNA Ligase. The mixture was incubated for 15 mins at 25° C. to yield the doubly-adapted DNA fragment product.

Step 12. Washing of Doubly-adapted Immobilized DNA Fragments

The doubly-adapted DNA-immobilized streptavidin coated magnetic particles were precipitated on a magnetic rack and the supernatant was removed. The beads were washed twice, by re-suspending in a high stringency wash buffer (0.1×SSC, 0.1×SDS). The beads were finally washed with 1× VERASEQ™ Buffer (25 mM TAPS, 50 mM KCl, 2 mM $MgCl_2$, 1 mM β-ME, pH 9.3 at 25° C.).

Step 13. On-bead UDG/Endonuclease VII Digestion of Immobilized Doubly Adapted DNA Fragments The washed doubly-adapted DNA-immobilized streptavidin beads were re-suspended in 1× VERASEQ™ buffer was treated with 1 U of thermolabile UDG and 10 U of Endonuclease VII for 20 mins at 37° C. before the UDG reaction was stopped by denaturating at 60° C. for 10 min. This treatment cuts the desired product from the bead. The streptavidin coated magnetic particles were precipitated on a magnetic rack and the supernatant was removed and retained for further PCR amplification. This final library of single stranded, doubly adapted fragments is referred to as an OmniPrep library.

Step 14. PCR Amplification of OmniPrep Libraries

PCR amplification of the OmniPrep libraries was performed on Agilent Surecycler 8800 thermocycler in 1× VERASEQ™ buffer supplemented with 125 µM of the forward PCR primer (Fwd_PCR_Primer_long), 125 µM of the reverse PCR primer (Rev_PCR_Primer_long), 500 µM dNTPs and 1 U of VERASEQ™ 2.0 DNA polymerase. Thermocycling conditions were 10 cycles of:

Denaturation at 95° C. for 30 sec
Annealing at 60° C. for 30 sec
Extension at 72° C. for 90 sec
Results The PCR products were loaded on to a 2% agarose gel and ran at 120 V for 60 mins (gel shown in FIG. 13). The results show that both an on-bead based variant of OmniPrep and the use of dATPαS instead of dATP are possible and add performance benefits to the ssDNA library construction method. Furthermore, nuclease treatment prior to ligation can be used to reduce potential contaminants and unwanted side-products (for example, adapter-dimer) while maintaining the integrity of the sample-prepped library.

The invention claimed is:

1. A method for preparing an amplified mixture of nucleic acid molecules wherein each amplified molecule in the mixture has a known region at each end, the method comprising:
   a) providing a sample containing a population of nucleic acid molecules,
   b) treating the population to produce first single stranded oligonucleotides of different sequence from each of the nucleic acid molecules in the population,
   c) joining a hairpin oligonucleotide sequence to each of the first single stranded oligonucleotides of different sequence using template independent nucleic acid polymerase, wherein the hairpin oligonucleotide sequence comprises a single stranded region comprising a 5'-triphosphate, a region of self-complementary double stranded sequence, a 3'-overhang which hybridises to the first single stranded oligonucleotide, and a blocking moiety at the 3' end,
   d) removing the 3' blocking moiety,
   e) producing a full length copy of each of the first single stranded oligonucleotides by extending the deblocked 3' hydroxyl of the hairpin oligonucleotide sequence to create a blunt end,
   f) attaching a further oligonucleotide sequence to each full length copy of the first single stranded oligonucleotides,
   g) cleaving the hairpin oligonucleotide sequence, thereby producing a mixture of double stranded nucleic acid molecules comprising the first single stranded oligonucleotides of different sequence and full length copies thereof, wherein each full length copy thereof has a known region at each end, and
   h) amplifying the double stranded nucleic acid molecules of step g), thereby generating an amplified mixture of nucleic acid molecules wherein each amplified molecule in the mixture has a known region at each end.

2. The method of claim 1 wherein the template independent nucleic acid polymerase enzyme is terminal transferase or polyadenylate polymerase (PAP).

3. The method of claim 1 wherein the hairpin oligonucleotide sequence comprises a triphosphate moiety attached to the 5'-end via a linker.

4. The method of claim 1 wherein the first single stranded oligonucleotide is copied using a nucleic acid polymerase or reverse transcriptase.

5. The method according to claim 1 wherein first single stranded oligonucleotides are DNA strands or RNA strands.

6. The method according to claim 3 wherein the linker comprises a ribose or deoxyribose moiety and the oligonucleotide is attached via the nucleotide base.

7. The method according to claim 1 wherein the first single stranded oligonucleotides are obtained by chemical or enzymatic cleavage of the sample.

8. The method according to claim 7 wherein the first single stranded oligonucleotides are obtained using bisulfite treatment.

9. The method according to claim 7 wherein the first single stranded oligonucleotides are a pool of fragments derived from treating a nucleic acid sample with an enzyme.

10. The method of claim 1 wherein the attaching is via ligation.

11. The method according to claim 1 wherein the hairpin oligonucleotide sequence is attached to a solid support.

12. The method according to claim 1 wherein the hairpin oligonucleotide sequence carries a moiety for attachment to a solid support, and the joined first single stranded oligonucleotides of different sequence and hairpin oligonucleotide sequence are immobilised.

13. The method of claim 1 wherein the blocking moiety at the 3' end is a phosphate.

14. The method of claim 13 wherein the phosphate is removed using a suitable kinase to release an extendable 3' hydroxyl.

* * * * *